United States Patent
Chen et al.

(10) Patent No.: US 10,227,601 B2
(45) Date of Patent: Mar. 12, 2019

(54) PTDUF266 GENE REGULATING CELL WALL BIOSYNTHESIS AND RECALCITRANCE IN POPULUS

(71) Applicant: UT-Battelle, LLC, Oak Ridge, TN (US)

(72) Inventors: Jin-Gui Chen, Oak Ridge, TN (US); Sara Jawdy, Oak Ridge, TN (US); Xiaohan Yang, Knoxville, TN (US); Gerald A. Tuskan, Oak Ridge, TN (US); Yongil Yang, Oak Ridge, TN (US); Lee E. Gunter, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 15/687,818

(22) Filed: Aug. 28, 2017

(65) Prior Publication Data

US 2018/0057834 A1  Mar. 1, 2018

Related U.S. Application Data

(60) Provisional application No. 62/382,435, filed on Sep. 1, 2016.

(51) Int. Cl.
*C12N 15/82* (2006.01)
*C12P 7/06* (2006.01)
*C07K 14/415* (2006.01)
*C12P 7/10* (2006.01)

(52) U.S. Cl.
CPC ........ *C12N 15/8245* (2013.01); *C07K 14/415* (2013.01); *C12N 15/8213* (2013.01); *C12N 15/8217* (2013.01); *C12N 15/8218* (2013.01); *C12N 15/8246* (2013.01); *C12N 15/8255* (2013.01); *C12N 15/8261* (2013.01); *C12P 7/06* (2013.01); *C12P 7/10* (2013.01); *C12P 2203/00* (2013.01)

(58) Field of Classification Search
None
See application file for complete search history.

(56) References Cited

U.S. PATENT DOCUMENTS

2006/0107345 A1* 5/2006 Alexandrov ......... C07K 14/415
800/278

OTHER PUBLICATIONS

Tuskan et al., NCBI, GenBank Sequence Accession No. XM_002317104.2; Published Dec. 31, 2013.*
Melani A. Atmodjo, et al., "Evolving Views of Pectin Biosynthesis," Annu. Rev. Plant Biol., 2013, pp. 747-779, vol. 64.
Melani A. Atmodjo, et al., "Galacturonosyltransferase (GAUT)1 and GAUT7are the core of a plant cell wall pectin biosynthetic homogalacturonan:galacturonosyltransferase complex," PNAS Early Edition, 2011, pp. 1-6, www.pnas.org/cgi/doi/10.1073/pnas.1112816108.
Brandi L. Cantarel, et al., The Carbohydrate-Active EnZymes database (CAZy): an expert resource for Glycogenomics, Nucleic Acids Research, 2009, pp. D233-D238, vol. 37.
Christelle Breton, et al., "Structures and mechanisms of glycosyltransferases," Glycobiology. 2006, pp. 29R-37R, vol. 16 No. 2.
Kerry H. Caffall, et al., "*Arabidopsis thaliana* T-DNA Mutants Implicate GAUT Genes in the Biosynthesis of Pectin and Xylan in Cell Walls and Seed Testa," Molecular Plant, 2009, pp. 1000-1014, vol. 2, No. 5.
Nick Carpita, et al., "Molecular biology of the plant cell wall: searching for the genes that define structure, architecture and dynamics," Plant Molecular Biology, 2001, pp. 1-5, vol. 47.
Kanwarpal S. Dhugga, "Building the wall: genes and enzyme complexes for polysaccharide synthases," Current Opinion in Plant Biology, 2001, pp. 488-493, vol. 4.
Jack Egelund, et al., "*Arabidopsis thaliana* RGXT1 and RGXT2 Encode Golgi-Localized (1,3)-a-D-Xylosyltransferases Involved in the Synthesis of Pectic Rhamnogalacturonan-II," The Plant Cell, 2006, pp. 2593-2607, vol. 18.
Robert D. Finn, et al., "The Pfam protein families database: towards a more sustainable future," Nucleic Acids Research, 2016, pp. D279-D285, vol. 44.
Sara Fasmer Hansen, et al., Plant glycosyltransferases beyond CAZy: aperspective on DUF families, Frontiers in Plant Science, 2012, pp. 1-10, vol. 3, Article 59.
Sara Fasmer Hansen, et al., "Exploring genomes for glycosyltransferases," The Royal Society of Chemistry, 2010, pp. 1773-1781, vol. 6.
Jesper Harholt, et al., "ARAD proteins associated with pectic Arabinan biosynthesis form complexes when transiently overexpressed in planta," Planta, 2012, pp. 115-128, vol. 236.
Jesper Harholt, et al., "Arabinan Deficient 1 Is a Putative Arabinosyltransferase Involved in Biosynthesis of Pectic Arabinan in *Arabidopsis*," Plant Physiology, 2006, pp. 49-58, vol. 140.
Ho-Yon Hwang, et al., "The Caenorhabditis elegans Genes sqv-2 and sqv-6, Which Are Required for Vulval Morphogenesis, Encode Glycosaminoglycan Galactosyltransferase II and Xylosyltransferase," The Journal of Biological Chemistry, 2003, pp. 11735-11738, vol. 278, No. 14.
Jacob Kruger Jensen, et al., "Identification of a Xylogalacturonan Xylosyltransferase Involved in Pectin Biosynthesis in *Arabidopsis*," The Plant Cell, 2008, pp. 1289-1302, vol. 20.

(Continued)

*Primary Examiner* — Vinod Kumar
(74) *Attorney, Agent, or Firm* — Edna I. Gergel

(57) ABSTRACT

This disclosure provides genetically modified plants having desirable levels of sugar release, cellulose content and reduction of recalcitrance; methods of genetically modifying plants to modulate sugar release, cellulose and lignin contents; and uses of such plants. The inventors have determined that genetic modification of PdDUF266A from *Populus*, encoded by locus Potri.011G009500 resulted in transgenic *Populus* trees with changes in lignin and cellulose content as well as altered sugar release phenotypes. Plants with altered sugar release, cellulose and lignin content, based on modulation of the expression or activity of the PdDUF266A gene, have diverse uses including pulp and paper production, and biofuel and bioproducts production.

7 Claims, 6 Drawing Sheets
(2 of 6 Drawing Sheet(s) Filed in Color)

Specification includes a Sequence Listing.

(56) References Cited

OTHER PUBLICATIONS

Eva Knoch, et al., "A b-glucuronosyltransferase from *Arabidopsis thaliana* involved in biosynthesis of type II arabinogalactan has a role in cell elongation during seedling growth," The Plant Journal, 2013, pp. 1016-1029, vol. 76.

Jeemeng Lao, et al., "The plant glycosyltransferase clone collection for functional genomics," The Plant Journal, 2014, pp. 517-529, vol. 79.

Shundai Li, et al., "Cellulose Synthesis and Its Regulation," The *Arabidopsis* Book published by The American Society of Plant Biologists, 2014, pp. 1-22.

Chu-Yu Ye, et al., "Comparative analysis of GT14/GT14-like gene family in *Arabidopsis, Oryza*, Populus, Sorghum and Vitis," Plant Science, 2011, pp. 688-695, vol. 181.

April Jennifer Madrid Liwanag, et al., "Pectin Biosynthesis: GALS1 in *Arabidopsis thaliana* Is a b-1,4-Galactan b-1,4-Galactosyltransferase," The Plant Cell Preview, American Society of Plant Biologists, 2012, pp. 1-13.

Richa Mudgal, et al., "De-DUFing the DUFs: Deciphering distant evolutionary relationships of Domains of Unknown Function using sensitive homology detection methods," Biology Direct, 2015, pp. 1-23, vol. 10, Issue 38.

Bent Larsen Petersen, et al., "Assay and heterologous expression in Pichia pastoris of plant cell wall type-II membrane anchored glycosyltransferases," Glycoconj J, 2009, pp. 1235-1246, vol. 26.

Emilie A Rennie and Henrik Vibe Scheller, Xylan biosynthesis, Current Opinion in Biotechnology, 2014, pp. 100-107, vol. 26.

Henrik Vibe Scheller and Peter Ulvskov, "Hemicelluloses," Annu. Rev. Plant Biol., 2010, pp. 263-289, vol. 61.

Jiunn-Chern Yeh, et al., "Molecular Cloning and Expression of a Novel b-1,6-NAcetylglucosaminyltransferase That Forms Core 2, Core 4, and I Branches," The Journal of Biological Chemistry, 1999, pp. 3215-3221, vol. 274, No. 5.

Yihua Zhou, et al., "BC10, a DUF266-containing and Golgi-located type II membrane protein, is required for cell-wall biosynthesis in rice (*Oryza sativa* L.)," The Plant Journal, 2009, pp. 446-462, vol. 57.

* cited by examiner

PTDUF266 GENE REGULATING CELL WALL BIOSYNTHESIS AND RECALCITRANCE IN POPULUS

CROSS REFERENCE TO RELATED APPLICATIONS

This application claims priority from U.S. Provisional Application No. 62/382,435 filed Sep. 1, 2016, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in the ASCII text file, named as Sequence_Listing_3420_1_ST25.txt of 121 KB and created on Aug. 17, 2017, and submitted to the United States Patent and Trademark Office via EFS-Web, is incorporated herein by reference.

BACKGROUND

The structural polysaccharides such as cellulose, lignin and hemicellulose are major components of plant cell walls. Over 2,000 genes have been estimated to be required for these polysaccharide biosynthesis, assembly and structural maintenance.

Glycosyltransferases (GTs) were regarded as an important family of proteins participating in the synthesis of polysaccharides by transferring sugar moieties from an activated nucleotide sugar to a specific acceptor molecule. Based on the amino acid sequence similarity, GT has been classified into 99 families designated as GT1 to GT99. These classifications are available in the carbohydrate active enzyme (CAZy) database (hhttp://www.cazy.org/GlycosylTransferases.html).

Pectin, hemicellulose and cellulose have been shown to be synthesized by at least one of GT members as summarized in three recent review articles. Galacturonosyltransferase (GAUT) 1, 7 and 8 that were classified as GT8 group members synthesize homogalacturonan of a pectin type among three different pectin polysaccharide types. Other pectin polysaccharide types of Rhamnoglacturonan I and II synthesized by arabinosyltransferase (ARAD) of GT47, galactosyltransferase (GAL) GT92, and xylosyltransferase of rhamnogalacturonan II (RGXT) of GT77 group. Xylogalacturonan synthesis, the third pectin polysaccharide type, was regulated by xylosyltransferase (XGD1) classified in GT47-C. Hemicellulose biosynthesis is regulated by CELLULOSE SYNTHASE-LIKE PROTEIN (CSL), IRREGULAR XYLEM (IRX) and CELL WALL MUTANT (MUR).

Most of these biosynthetic enzymes have been shown to localize to the Golgi apparatus, and all of them have predicted type II transmembrane topology. Although most GTs have specific activity synthesizing one of cell wall components, cellulose synthase (CESA) and CSL that were generally classified as GT2 and GT34, respectively, shared their activity both in cellulose and hemicellulose synthesis.

About 1.7% of *Arabidopsis* annotated genes were predicted as GTs but less than 20% of them were grouped into 42 GT groups.

An *Arabidopsis* GT14 member (AtGlcAT14A) was recently shown to function as β-glucuronosyltransferase involved in type II arabinogalactan synthesis. Domain of Unknown Function 266 (DUF266)-containing proteins (DUF266 proteins) share amino acid similarity with GT14 proteins but Pfam database annotates DUF266 as a plant-specific domain and predicts them as 'likely to be GT related'. In *Arabidopsis*, a total of 14 DUF266 proteins (AtDUF266) were distantly related to GT14 group family. Recently, a total of 22 AtDUF266 proteins were identified by phylogenetic analysis of full-length amino acid sequences. Twenty-seven *Populus* DUF266 proteins (based on *P. trichocarpa* annotation v2.0) were also classified as GT14-LIKE proteins in this phylogenetic analysis. Again, these DUF266/GT14-LIKE proteins formed a cluster that was phylogenetically distinct from the GT14 family members. Subsequently, AtDUF266 proteins were categorized as 'not classified GT (GTnc)', to better reflect the uncharacterized features of this protein subfamily. The only characterized DUF266 protein is rice BRITTLE CULM 10 (OsBC10) which has amino acid similarity with 2 β-1,6-N-acetylgalactosyltransferase (C2GnT) in animals.

In vitro enzymatic assay using Chinese hamster ovary cells revealed that OsBC10 has galactosyltransferase activity that is only ~1% of animal C2GnT. Rice natural variants of OsBC10 displayed phenotypic abnormalities such as small size of plant body and tiller number and brittleness of plant body. Glucose content was decreased in Osbc10 mutant, and xylose, arabinose and lignin contents were increased, indicating that OsBC10 influences cell wall composition. OsBC10 was predicated to be a type II intercellular membrane binding protein and was shown to be localized in the Golgi complex.

Except OsBC10, no other DUF266 proteins have been functionally characterized. Thus, the function of a large number of GTs remains elusive. For worldwide requirement to replace fossil transportation fuel, plant biomass is spotlighted as an alternative energy source. Efficient sugars release such as glucose and xylose from plant biomass is a pivotal factor to produce abundant useful biofuel.

BRIEF SUMMARY OF THE DISCLOSURE

This disclosure provides genetically modified plants characterized by an altered expression of the PdDUF266A (Potri.011G009500) as compared to a control plant. In some embodiment, the altered expression is increased expression of the PdDUF266A (Potri.011G009500) gene. In other embodiment, the altered expression is a decreased expression of the PdDUF266A (Potri.011G009500) gene.

In some embodiments, the genetically modified plants belong to a genus selected from the group consisting of *Populus, Manihot, Gossypium, Eucalyptus, Medicago, Arabidopsis, Solanum, Oryza* and *Zea*.

In specific embodiments, the genetically modified plants are selected from the group consisting of *Populus balsamifera, Populus deltoides, Populus trichocarpa, Populus tremuloides, Populus tremula, Populus alba* and *Populus maximowiczii*.

In some embodiments, the reduction in PdDUF266A gene expression is achieved by a method selected from the group consisting of introducing a nucleic acid inhibitor, the CRISPR/Cas system, the Cre/Lox system, the TALEN system, and homologous recombination.

In some specific embodiments, a nucleic acid inhibitor is selected from the group consisting of an antisense RNA, a small interfering RNA, an RNAi microRNA, an artificial microRNA, and a ribozyme.

In another aspect, this disclosure provides improved methods of producing biofuels comprising using a genetically modified plant characterized by an induced expression of the PdDUF266A (Potri.011G009500) gene.

In yet another aspect, this disclosure provides an expression comprising a nucleotide sequence that is transcribed into a nucleic acid inhibitor of expression of the PdDUF266A (Potri.011G009500) gene, operably linked to a regulatory region that is functional in a plant, wherein the nucleic acid inhibitor is selected from the group consisting of an antisense RNA, a small interfering RNA, an RNAi microRNA, an artificial microRNA, and a ribozyme.

In some embodiments, the regulatory region comprises an inducible promoter or a tissue-specific promoter. In a specific embodiment, the tissue-specific promoter is a xylem-specific promoter.

In some embodiments, this disclosure provides methods for increasing glucose and/or xylose release in a plant or plant cell, comprising introducing into said plant or plant cell an expression vector for overexpression of the PdDUF266A (Potri.011G009500) gene operably linked to a regulatory region that is functional in said plant or plant cell, and expressing the nucleic acid in said plant or plant cell.

In other embodiment, this disclosure provides methods for increasing lignin content in a plant or plant cell, comprising introducing into said plant or plant cell an expression vector comprising a nucleotide sequence that is transcribed into a nucleic acid inhibitor of expression of the PdDUF266A (Potri.011G009500) gene operably linked to a regulatory region that is functional in said plant or plant cell, and expressing the nucleic acid in said plant or plant cell Furthermore, this disclosure provides a plant or plant cell genetically modified to comprise an expression vector disclosed herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Definitions

Figure 1:
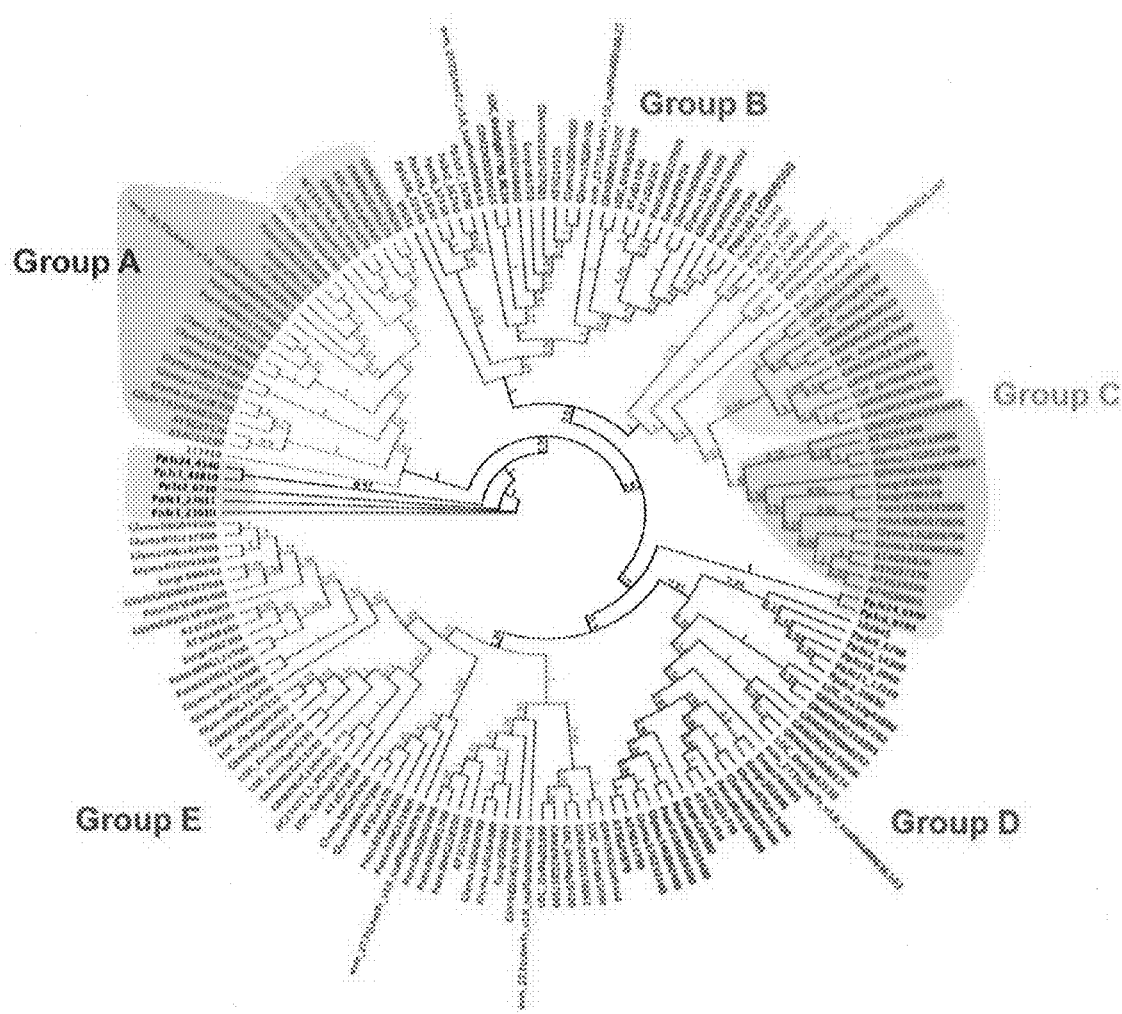
FIG. 1. Phylogenetic analysis of PdDUF266A (Potri.011G009500). A total of 169 DUF266 proteins were collected by amino acid sequence similarity analysis through Phytozome (v11.0) (https://phytozome.jgi.doe.gov/pz/portal.html). These 169 DUF266 proteins with 300 to 500 amino acids in length were identified from *Populus*, grape, *Eucalyptus*, soybean, *Arabidopsis*, rice, maize, *Amborella*, lycophyte and moss. Shown is maximum likelihood phylogenetic tree constructed by using the mtREV model fitting method. aLRT SH-like branch support method was used to determine likelihoods of branch and node. PdDUF266A is marked in red font. Rice BC10 protein is indicated in blue font. Five groups (A to E) are classified by clustering. The clades containing the monocot-(highlighted by light red), dicot—(highlighted by light blue) and moss-specific (highlighted by light green) DUF266 proteins are highlighted.

Unless defined otherwise, all technical and scientific terms used herein have the same meaning as commonly understood by one of ordinary skill in the art to which this invention belongs.

As used herein, the term "about" refers to an approximately +/−10% variation from a given value.

An "altered level of gene expression" refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

The term "biofuel" refers to any type of fuel which is derived in any way from biomass. In some embodiments, the biofuel in the context of the present invention is a liquid biofuel. The biofuel may mainly comprise an extensively pure compound, thus, may be a biofuel comprising more than 95% of said compound and less than 5% of one or more other compound(s), of more than 80% of said compound and less than 20% of one or more other compound(s) or of more than 75% of said compound and less than 25% of one or more other compound(s). Alternatively, the biofuel may be a mixture of different compounds.

In some embodiments, the biofuel comprises one or more alcohol(s), one or more ester(s), one or more carbonic acid(s), one or more ketone(s), one or more aldehyde(s) or one and/or more terpene(s). In some embodiments, the biofuel comprises one or more alcohol(s), one or more ketone(s) (e.g., acetone), one or more aldehyde(s) and/or comprises one or more ester(s). In some embodiments, the biofuel comprises one or more alcohol(s) and/or comprises one or more ester(s). In some embodiments, the biofuel may comprise more than 50% (v/v), more than 70% (v/v), more than 80% (v/v), more than 90% (v/v) or more than 95% (v/v) of one or more alcohol(s). In some embodiments, these alcohols are aliphatic alcohols (e.g., methanol, ethanol, n-propanol, isopropanol and/or butanol), specifically aliphatic alcohols of the general molecular formula $H-C_nH_{2n}-OH$, even more specifically, one of the first four aliphatic alcohols with n=1-4 (i.e., methanol, ethanol, propanol and/or butanol). In the context of the present invention these alcohols may also be designated as "bioalcohols" (i.e., as "biomethanol", "bioethanol", "biopropanol" and "biobutanol"). Due to its chemical and technical characteristics, in the context of biofuel, butanol is sometimes also designated as "biogasoline". In some embodiments, the alcohol may be a di-, tri or polyalcohol such as, e.g., glycerol. In some embodiments, the biofuel in the context of the present invention comprises more than 50% (v/v), more than 70% (v/v), more than 80% (v/v), more than 90% (v/v), or more than 95% (v/v) ethanol. In a specific embodiment, the biofuel of the present invention comprises at least 90% (v/v) ethanol.

As used herein, the term "biomass" refers to any cellulosic or lignocellulosic raw material and includes materials containing cellulose, and optionally further containing hemicellulose, lignin, starch, oligosaccharides and/or monosaccharides.

The term "cellulose" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin).

The term "control plant" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "DNA," as used herein, refers to a nucleic acid molecule of one or more nucleotides in length, wherein the nucleotide(s) are nucleotides. By "nucleotide" it is meant a naturally-occurring nucleotide, as well as modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

As used herein, the term "fermentation" refers to the enzymatic and/or anaerobic breakdown of organic substances by microorganisms to produce simpler organic compounds such as alcohols. While fermentation may occur under anaerobic conditions, it is not intended that the term be solely limited to strict anaerobic conditions, as fermentation may also occur under aerobic (e.g., in the presence of oxygen) or microaerobic conditions.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically engineered" (or "genetically modified") refers to a microorganism comprising a manipulated genome or nucleic acids.

The term "hexose" refers to a monosaccharide with six carbon atoms, having the chemical formula $C_6H_{12}O_6$. Examples of hexose include glucose and fructose.

The term "homolog" means a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). "Type I glutamine synthetase (glnA) gene homolog" furthermore means that the function is equivalent to the function of the Type I glutamine synthetase (glnA) gene.

"Lignin", as used herein, refers to a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

Lignin "synthesis" or "biosynthesis" refers to the production of lignin in a plant, plant tissue, or plant cell. "Lignin synthesis characteristics" or "lignin biosynthesis characteristics" include the total amount of lignin ("lignin content") in a plant or plant cell, the ratio or amount of monolignol subunits, and expression and/or activity of lignin biosynthetic enzymes. Lignin content, ratio or amount of monolignols, and expression and/or activity of lignin biosynthetic enzymes, can be affected by modulation of the Potri.011G009500 gene, where one or more of these characteristics can be high or low relative to the same characteristic or characteristics in a plant that does not have the same modulation of the Potri.011G009500 gene.

As used herein, the term "nucleic acid" has its general meaning in the art and refers to a coding or non coding nucleic acid sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e. nuclear or mitochondrial).

A "nucleic acid inhibitor" is a nucleic acid that can reduce or prevent expression or activity of a target gene. For example, an inhibitor of expression of Potri.011G009500 can reduce or eliminate transcription and/or translation of the Potri.011G009500 gene product, thus reducing Potri.011G009500 protein expression.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

General Description

Disclosed herein are genetically modified plants having modified expression of the *Populus* Potri.011G009500 (PdDUF266A) gene. The *Populus* Potri..011G009500 (PdDUF266A) CDS gene sequence is shown in SEQ. ID. NO: 37, and the genomic sequence is shown in SEQ. ID. NO: 38. The inventors provide evidence herein for roles of the *Populus* Potri.011G009500 (PdDUF266A) gene in affecting cell wall chemistry. Without being limited to a particular viewpoint, it is believed that Potri.011G009500 is involved in higher order interactions of cell wall components. The inventors have shown that over expression of Potri.011G009500 resulted in an increase in sugar release in overexpressing transgenic lines compared to control plants when samples were subjected to a no pretreatment condition.

Potri.011G009500 Alleles, Allelic Variants and Homologs

The inventors have described herein a DUF266-containing protein from *Populus*, PdDUF266A, encoded by locus Potri.011G009500, whose altered expression resulted in transgenic *Populus* trees with changes in cellulose and lignin contents as well as altered sugar release phenotypes.

This disclosure also provides homologs of the polypeptide encoded by Potri.011G009500. A Potri.011G009500 homolog can be a homolog, ortholog or variant of the polypeptide having the amino acid sequence set forth in the Potri.011G009500 amino acid sequence shown in SEQ ID NO: 19. For example, a Potri.011G009500 homolog can have an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in the Potri.011G009500 amino acid sequence shown in SEQ ID NO: 19.

In some embodiments, a homolog of Potri.011G009500 is a functional homolog. A functional homolog is a polypeptide that has sequence similarity to the Potri.011G009500 amino acid sequence shown in SEQ ID NO: 19 and that carries out one or more of the biochemical or physiological function(s) of the polypeptide of the Potri.011G009500 amino acid sequence shown in SEQ ID NO: 19. A functional homolog may be a natural occurring polypeptide and the sequence similarity may be due to convergent or divergent evolutionary events. As such, functional homologs are sometimes designated in the literature as homologs or orthologs or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cell wall-modulating polypeptide or by combining domains from the coding sequences for different naturally-occurring cell wall-modulating polypeptides ("domain swapping"). The term "functional homolog" can also be applied to the nucleic acid that encodes a functionally homologous polypeptide.

A homolog of Potri.011G009500 can be a native Potri.011G009500 protein, i.e., one or more additional copies of the coding sequence for a Potri.011G009500 homolog that is naturally present in the cell. Alternatively, a homolog of Potri.011G009500 can be heterologous to the cell, e.g., a transgenic *Populus* plant can contain the coding sequence for a Potri.011G009500 homolog from an *Arabidopsis* plant, for example. Potri.011G009500 homologs from multiple species are identified in Table 2 (SEQ ID NOS: 26-36). Table 2 is shown below in Example 2. Furthermore, a Potri.011G009500 homolog in *Arabidopsis thaliana* has the Genbank Accession NP_683459 for the protein.

Modulation of the Potri.011G009500 Gene is Associated with Altered Sugar Release, and Lignin Content This disclosure further provides for modulation of the Potri.011G009500 gene. "Modulation" refers to changing the expression or activity of the Potri.011G009500 gene.

In one embodiment, the Potri.011G009500 gene can be modulated by increasing or decreasing expression of the gene itself. Methods to modulate expression are disclosed in detail below. In a specific embodiment, Potri.011G009500 gene is modulated by decreasing the expression of the gene.

Modulation of the Potri.011G009500 gene can lead to proteins with altered activity. "Altered activity" includes an increase or decrease in a known activity of a protein encoded by a gene of interest, including loss of an established or proposed function, or gain of a new function. For example, the inventors have determined that modulating the Potri.011G009500 gene, for example, by manipulating the expression of the Potri.011G009500, can affect cellulose and lignin content and/or sugar release.

Altered S/G ratios in a plant (e.g., *Populus* species) include, for example, alterations from essentially 50% syringyl ("S"): 50% guaiacyl ("G") units to essentially 100% syringyl units, or essentially 100% guaiacyl units. The terms "units" and "subunits" are used interchangeably herein. Specific S/G ratios include, for example, greater than 2:1, e.g., 2.1:1, 2.2:1, 2.5:1, 2.8:1, 3.0:1, 3.5:1, 4:1, etc., or less than 2:1, e.g., 0.5:1, 0.8:1, 1:1, 1.2:1, 1.5:1, 1.8:1, or 2:1.3, 2:1.5, 2:1.7, 2:1.9, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant. In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

By manipulating the Potri.011G009500 gene, the amount and/or rate of S subunit to G subunit biosynthesis, or the incorporation of S to G subunits into the lignin structure, can be altered. Alteration in the S/G subunit ratio alters the lignin composition of the plant cell wall. Manipulating the Potri.011G009500 gene can thus modulate the lignin composition of a plant.

G units have greater capacity for cross-linking between monomers relative to S units. Thus, increasing the ratio of S/G subunits to greater than 2:1 increases S subunits and decreases. G subunits in lignin and thus decreases cross-linking between subunits incorporated into lignin. This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in *Populus* at values above 2.0. The exact way this occurs is not known though it is speculated that lignin remains intact during saccharification under high temperature and/or pressure. Nevertheless, biomass with an S/G ratio above 2.0 releases more sugar.

"Sugar release" includes high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant or genetic modification. "Low" sugar release (i.e., high recalcitrance) means that sugar can be extracted less easily, or less sugar can be extracted, from a plant, under conditions that would result in more sugar release in a plant without the particular allelic variant or genetic modification. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Sugar release can be measured, for example, by saccharification analysis. In one example of saccharification analysis, sugars are extracted with alpha-amylase and β-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/ release, such as by addition of glucose oxidase/peroxidase for measuring glucose content, and/or xylose dehydrogenase to measure xylose content.

High or low sugar release can be an increase or decrease in sugar release or sugar recovery of 2%, 5%, 8%, 10%, 15%, 20%, 25%, 30%, 40%, 50%, 60%, 70%, 80%, 90%, or 100% in a plant with a particular modulation of the Potri.011G009500 gene, relative to sugar release or sugar recovery from a plant that does not have the modulation of the Potri.008G064000 gene. In one example, "low" glucose release is glucose release of less than 0.1, 0.15, 0.2, or 0.25 g glucose per g biomass. "High" glucose release is glucose release of 0.3, 0.35, 0.4, or 0.45 g glucose per g biomass or more. "Low" glucose/xylose release is combined release of glucose and xylose of less than 0.2, 0.25, 0.3, 0.35, or 0.4 g combined glucose/xylose per g biomass. "High" glucose/xylose release is combined release of glucose and xylose above 0.4, 0.45, 0.5, 0.55, or 0.6 g combined glucose/xylose per g biomass.

Lignin forms strong bonds with sugars and interferes with access to these carbohydrates, making it difficult to extract the plant's sugars contained in cellulose and hemicellulose. Differences in lignin content alter the sugar release properties of a plant in the extraction process. Lower lignin levels in a plant are associated with higher levels of sugar release, while higher lignin levels are associated with lower levels of sugar release. Thus, sugar release and lignin content can show an inverse correlation. In addition, the higher interactions of cell wall components (including lignins) also determine the amount of sugar that can be released.

In some embodiments, gene modulation is achieved using available gene targeting technologies in the art. Examples of gene targeting technologies include the Cre/Lox system (described in Kuhn, R., & M. Torres, R., 2002. *Transgenesis Techniques: Principles and Protocols*, 175-204.), homologous recombination (described in Capecchi, Mario R. 1989. *Science*, 244: 1288-1292), TALENs (described in Sommer et al., 2015. *Chromosome Research*, 23: 43-55, and Cermak et al., 2011. *Nucleic Acids Research: gkr*218.), and CRISPR Cas system as described in Ran F A et al., 2013. *Nature Protocols*.

In one embodiment, Potri.011G009500 (PdDUF266A) modulation is achieved by a CRISPR/Cas system. CRISPR-Cas and similar gene targeting systems are well known in the art with reagents and protocols readily available (Mali, P. et al., 2013. *Science*, 339(6121), 823-826; Hsu, P. D. et al., 2014. *Cell*, 157.6: 1262-1278; Jiang et al., 2013. *Nature Biotechnology*, 31, 233-239). Exemplary genome editing protocols are described in Jennifer Doudna, and Prashant Mali, 2016. *"CRISPR-Cas: A Laboratory Manual"* (CSHL Press, ISBN: 978-1-621821-30-4) and Ran, F. Ann, et al. 2013. *Nature Protocols*, 8 (11): 2281-2308.

A CRISPR endonuclease comprises two components: (1) an RNA-dependent nuclease, typically microbial Cas9; and (2) a short "guide RNA" (gRNA or sgRNA) comprising a ~20 nucleotide targeting sequence that directs the nuclease to a location of interest in the genome. When co-expressed with an artificial sgRNA targeting a cellular gene, the Cas9 endonuclease generates double-stranded breaks of DNA at the targeted locus. In addition, when CRISPR endonuclease is supplemented with a stretch of DNA template homologous to the break region, the break is repaired using the supplied homologous DNA template via the process of homologous recombination (HR). CRISPR-mediated HR makes it possible to specifically edit the target DNA sequence and/or alter gene expression.

In one embodiment, modulation of the Potri.011G009500 (PdDUF266A) gene is achieved by site-directed mutagenesis to create mutant gene with altered gene expression. Site-directed mutagenesis is described in *Molecular Cloning*, 3rd Ed., *Current Protocols in Molecular Biology*, and U.S. patent application Ser. No. 12/442,143

Inhibitors and Expression Vectors for Modulating the Activity or Expression of Potri.011G009500

Further disclosed herein are nucleic acid inhibitors of expression of Potri.011G009500, or inhibitors of expression of allelic variants of Potri.011G009500, which can be used to reduce expression of the Potri.011G009500 gene and allelic variants thereof, to provide high lignin content, and/or altered SIG ratio. Specific nucleic acid inhibitors include antisense RNA, small interfering RNA, RNAi, microRNA, artificial microRNA, and ribozymes.

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., 2000. *Plant Cell Rep. V*19:304-310; Chang and Yang, 1996. *Bot. Bull. Acad. Sin., V*37:35-40 and Han et al., Biotechnology in Agriculture and Forestry, V44:291 (ed. by Y. P. S. Bajaj), Springer-Vernag, (1999).

Nucleic Acid Inhibitors

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit Potri.011G009500 expression in plants. Suitable nucleic acid inhibitors, i.e., nucleic acids capable of inhibiting the expression of a target gene, include full-length nucleic acids of allelic variants of Potri.011G009500, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators of Potri.011G009500 and Uses Thereof.

This disclosure provides methods of altering cellulose and lignin contents and sugar release in a plant, comprising introducing into a plant cell an exogenous nucleic acid vector comprising a nucleotide sequence that is transcribed into overexpression of the PdDUF266A gene operably linked to a regulatory region that is functional in a plant as described above, where a tissue of a plant produced from the plant cell has an altered cell wall compared to the cell wall in tissue of a control plant that does not comprise the nucleic acid inhibitor.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab IR promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis* SUC2 sucrose-H+ symporter promoter (Truernit et al., *Planta*, 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)) and the rice tungro bacilliform virus (RTBV) promoter (Dai et al., *Proc. Natl. Acad Sci. USA*, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Transgenic Plants/Plant Species/Plant Cells

Also disclosed herein are plants and plant cells genetically modified by introduction of overexpression of PdDUF266A. In other embodiment, also disclosed herein are plants and plant cells genetically modified by introduction of the disclosed inhibitors of expression.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous Potri.011G009500 allelic variant whose expression has not previously been confirmed in particular recipient cells.

Initial and immediate application of the expression of Potri.011G009500 allelic variants can be made in the bioenergy crops *Populus* and switchgrass, but the application can be extended to other bioenergy crops such as corn, other sources of lignocellulosic biomass and other model plants e.g., *Salix, Miscanthus*, rice and *Medicago*.

For example, the vectors described herein can be used to transform a number of monocotyledonous and dicotyledonous plants and plant cell systems, including alfalfa, ash, beech, birch, canola, cherry, clover, cotton, cottonseed, *eucalyptus*, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, sorghum, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera Acer, Afzelia, *Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In one aspect, a plant cell comprising a Potri.011G009500 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of Potri.011G009500 or a Potri.011G009500 allelic variant. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered lignin content, sugar release and cell wall structure.

Methods of Use of Transgenic Plants

Disclosed herein are methods to increase glucose and/or xylose release in a plant or plant cell, or to alter lignin content, by expressing the disclosed inhibitors in plants and plant cells.

Further improved methods of producing biofuel from cellulosic biomass, by using plants with increased expression or activity of the Potri.011G009500 gene in biofuel production processes. Methods of pretreatment and saccharification of biomass to fermentable sugars, followed by fermentation of the sugars to ethanol, are known in the art.

Articles of Manufacture

The materials and methods described herein are useful for modifying biomass characteristics, such as characteristics of biomass renewable energy source plants. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide altered lignin content in one or more tissues of plants grown from such seeds.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Materials and Methods

Phylogenic and Sequence Analysis

To identify DUF266 proteins in *Populus*, the full-length amino acid sequence of an *Arabidopsis* DUF266 protein, AT1G62305, was subjected to protein homolog search integrated in the Phytozome v11.0 (https://phytozome.jgi.doe-.gov) (Goodstein et al, 2012, Nucleic Acids Res. 40, D1178-1186). Each identified PtDUF266 homolog was then used as a new query to search for DUF266 proteins in moss (*Physcomitrella patens*), lycophyte (*Selaginella moellendorfii*), rice (*Oryza saliva*), corn (*Zea mays*), soybean (Glycine max), *Amborella* (*Amborella trichopoda*), grape (*Vitis vinifera*), *Arabidopsis* (*Arabidopsis thaliana*) and *Eucalyptus* (*Eucalyptus grandis*) genomes. Identified DUF266 proteins from each species were subsequently used to perform reciprocal homolog search till no new DUF266 protein could be identified. The full-length amino acid sequences with >30% similarity (e-value <0.01) to each input protein were selected and subjected to Pfam database (Finn et al., 2016, Nucleic Acids Res. 44, D279-285) to validate the presence of the core-2/I branching domain, a hallmark of DUF266 proteins, and other possible motifs. The transmembrane domain (TM) was predicted by using web-based TMHMM v2.0 (www.cbs.dtu.dk/servies/TMHMM) (Kroge et al., 2001, J. Mol. Biol. 305, 567-580). A probability value of 0.8 was used as a criterion to determine the presence of TM.

Protein sequences of *Populus trichocarpa* DUF266 were collected from Phytozome v11 [available at the Plant Comparative Genomics portal of the Department of Energy's Joint Genome Institute website]: *Populus trichocarpa* v3.0. All other PtDUF266 sequences from other plant species were collected from Phytozome v 11.0, too. To conduct phylogenetic analysis, maximum likelihood (ML) tree was constructed with fill-length amino acid sequences of collected DUF266 proteins. Compiled DUF266 proteins were aligned together by using the MUSCLE software (Edgar, 2004, Nucleic Acids Res. 32, 1792-1797) integrated in the Geneious software (v8.1.2; Biomatters Ltd., New Zealand) with 12 maximum number of iterations together with kmer6_6 of distance measurement protocol under neighborhood joining clustering method. The best fitting model to construct maximum likelihood was calculated by ML option integrated in the MEGA 7 software (Kumar et al., 2016, Mol, Biol. Evol. 33, 1870-1874.). The phylogenetic tree was constructed by selecting the model with the lowest value of Akaike Information Criterion (AIC) and Bayesian Information Criterion (BIC), and Maximum Likelihood values (InL). aLRT SH-like branch support method was used to improve likelihoods of branch and node.

Generation of Transgenic Plants

The full-length open reading frame of PdDUF266A was amplified from *Populus deltoides* WV94. The complementary DNA (cDNA) was cloned into the pAGW560 binary vector in which the expression of PdDUF266A was driven by the UBIQUITIN 3 promoter. *Agrobacterium*-mediated transformation into *P. deltoides* genotype WV94 was conducted at ArborGen Inc. (Ridgeville, S.C.) as described previously (Biswal et al., 2015, *Biotechnol. Biofuels*, 8, 41). A total of eight independent transformation events or lines were obtained, along with five ramets for each transgenic event, together with equal numbers of ramets for empty vector transformed control plants, were propagated at Oak Ridge National Laboratory greenhouses at constant 25° C. and 16-h day length. All plants were initially grown in Leach tubes and transferred to larger pots, and after six months of growth, plant height and stem diameter were measured, stem samples were collected and air-dried for cell wall chemistry analyses.

qRT-PCR Assays

To perform quantitative analysis of PdDUF266A transcript in the *Populus* transgenic plants, total RNA was extracted from the petiole, leaf blade of mature leaf and stem (internodes 6 to 9) of 6-month-old plants grown in the greenhouse by using Sigma spectrum plant RNA extraction kit with modified Cetyltrimethyl Ammonium Bromide (CTAB) extraction buffer (Sigma-Aldrich, St. Louis, Mo.). One μg of total RNA was used to generate cDNA by using the Rite aid reverse transcriptase following manufacturer's instruction (Thermo Fisher Scientific, Hudson, N.H.). DreamTaq enzyme solution mixture (Thermo Fisher Scientific) was used for PCR reaction together with 1 μl of 2× diluted cDNA and gene-specific primers (Additional file 1). Gene-specific primers were designed from non-conserved DNA sequence region based on ClustalW DNA sequence alignment of PdDUF266A and its paralogs including Potri.002G227000, Potri.001G348400 and Potri.015G045500 (Thompson et al., 1994, Nucleic Acids Res. 22, 4673-3680). PCR reaction was performed as follows: denaturation at 95° C. for 2 min followed by 35 cycle of 95° C. for 30 second, 56° C. for 30 second and 72° C. for 20 second. Another step of 72° C. for 7 min was performed for final extension reaction. Amplification of *Populus* UBIQUITIN C gene (PdUBCc, Potri.006G205700) was used as a control by the same PCR reaction but replacing annealing stage with 57° C. and cycle number of 25. The PCR product was run on 1% agarose gel with TBE (45 mM Tris-borate, 1 mM EDTA) at 100V for 30 min. Gel image was taken by ChemiDoc XRS+ software (BIO-RAD, Hercules, Calif.).

For the expression pattern analysis of PdDUF266A in different tissues and organs, samples were collected between 12:00 PM and 2:00 PM from three WV94 plants (*Populus deltoides*). Total RNAs were extracted from root, young leaf, mature leaf, young stem (internodes 1 to 3), mature stem (internodes 6 to 8), petiole of mature leaf, phloem (bark of mature stem) and xylem (scrapped stem under bark of mature stem) by the same method as described above.

Cell Wall Chemical Composition Analysis

The dried stem of 6-month-old *Populus* transgenic and wild type (WV94) plants were used for cell wall chemical composition analysis. The size of stem samples was reduced to 40 mesh by Wiley-mill (Thomas Scientific, Swedesboro, N.J.) and Soxhlet-extracted with ethanol/toluene (1:2, v/v) for 24 h. The extractive-free sample was analyzed by the method consisting of two-step sulfuric acid ($H_2SO_4$) hydrolysis [34]. In the first-step, the extractive-free sample was hydrolyzed with 72% (w/w) $H_2SO_4$ at 30° C. for 1 h. In the second-step, the hydrolyzed sample was diluted to 4% $H_2SO_4$ (w/w) of final concentration, followed by autoclaving at 121° C. for 1 h. The hydrolysate was filtered from solid residue. The filtered liquid fraction was subjected to Dionex ICS-3000 ion chromatography system (Thermo Fisher Scientific, Sunnyvale, Calif.) for quantifying sugar contents. Total lignin content was quantified with acid soluble and insoluble lignin separation from hydrolysate and solid residue, respectively. Acid soluble lignin was measured with liquid fraction at 240 nm wave length using UV/Vis spectroscopy. Acid insoluble lignin was quantified with the filtered solid residue as described in the NREL procedure. All analyses were technically duplicated from two different plants of the same transgenic line for statistical analysis.

For Anthrone assay, the mature stem tissue (internodes 6 to 9) of 6-month-old *Populus* transgenic and WV94 plants grown in greenhouse were dried and milled. A total of 15 mg of milled sample were dissolved in 500 μl of acetic nitric acid reagent [1:8:2 (v/v) of nitric acid:acetic acid:water] (Sigma-Aldrich) to measure the cellulose content according to the Updegraff's method (Updegraff, 1969, Anal. Biochem. 32, 420-424). Heating was followed at 98° C. for 30 min. Insoluble fraction was pelleted by centrifugation for 10 min at 14,000 rpm. Six hundred μl of 67% sulfuric acid was added to the pellet followed by 1 h incubation at room temperature. Another centrifugation was performed for 5 min at 14,000 rpm to separate the solvent phase. One hundred eighty μl of deionized water was added to 20 μl solvent phase. Then 5× dilution was conducted. The freshly prepared anthrone solution (0.5 mg of anthrone/ml of concentrated sulfuric acid; Sigma-Aldrich) was mixed with the diluted solution. The mixture was boiled at 96° C. for 10 min followed by cooling down immediately at 4° C. The absorbance was measured at 630 nm wave length by SpectraMax Plus 384 microplate reader (Molecular devices, Sunnyvale, Calif.). The glucose content was determined by using the glucose standard curve. The cellulose content percentage was calculated by applying the glucose content to the equation of [(Glucose quantity×600 (dilution factor))/[15 (initial sample amount)×1000]]×100. All analyses were technically repeated three times with two different plants of the same transgenic line.

Saccharification Assay

Dried and Wiley-milled *Populus* stem (40 mesh) was used for sugar release measurement. About 250 mg of *Populus* sample (oven-dry weight) was loaded in 50 mM citrate buffer solution (pH 4.8) with Novozymes CTec2 (70 mg protein per gram of biomass; Franklinton, N.C.). The enzymatic hydrolysis was carried out at 50° C. with 200 rpm in an incubator shaker. Liquid hydrolysate was periodically collected at 0, 6, 12, 24, 48, and 72 h, and enzymes in the hydrolysate were deactivated in the boiling water before carbohydrates analysis. Released sugars in each hydrolysate were measured using Dionex ICS-3000 ion chromatography system. Each analysis was conducted in three technical replicates from single plant of each transgenic line.

Example 2: Phylogenetic Analysis of *Populus* DUF266A

DUF266 proteins have only been reported in the plant kingdom. However, little is known about their functions and the evolutional relationship of this protein family in different plant species remained elusive. In order to explore the function of DUF266 proteins, it was necessary to start with bioinformatics analysis. We identified DUF266 proteins from 10 plant species including moss (*P. patens*), lycophyte (*S. moellendorffii*), rice (*O. sativa*), corn (*Z. mays*), soybean (*G. max*), Amborella (*A. thrichopoda*), grape (*V. vinifera*), *Eucalyptus* (*E. grandis*), *Populus* (*P. trichocarpa*) and *Arabidopsis* (*A. thaliana*) by searching for proteins with amino acid similarity with AT1G62305, a previously reported DUF266 protein (Hansen et al., 2010, Mol. Biosyst. 6, 1773-1781). All identified DUF266 proteins had conserved core-2/I-branching domain which was designated as PF02485 domain in Pfam. A total of 187 DUF266 proteins were identified from 10 plant genomes. The average amino acid length was 378 but the number of DUF266 proteins varied among plant species. In the updated *Populus trichocarpa* genome annotation (v3.0), 25 *Populus* loci have been identified as DUF266 proteins in the present study. Identified *Populus* DUF266 proteins are listed in Table 1. Besides TM and DUF266, no other functional domain was predicted in the protein domain analysis.

TABLE 1

The list of *Populus trichocarpa* DUF266 and their GenBank accession numbers

| Potri.ID (v3.0) | Genebank_ID | SEQ ID NO |
| --- | --- | --- |
| Potri.001G188200 | XP_006369205 | 1 |
| Potri.001G195900 | XP_006369242 | 2 |
| Potri.001G215400 | XP_002298263 | 3 |
| Potri.001G348400 | XP_002300039 | 4 |
| Potri.002G227000 | XP_006387659 | 5 |
| Potri.003G001700 | XP_006385195 | 6 |
| Potri.003G002400 | XP_006385195 | 7 |
| Potri.003G002700 | XP_006385199 | 8 |
| Potri.004G097700 | XP_002305172 | 9 |
| Potri.004G228100 | XP_006385074 | 10 |
| Potri.006G076600 | XP_011019987 | 11 |
| Potri.006G233400 | XP_002309520 | 12 |
| Potri.008G018600 | XP_002311939 | 13 |
| Potri.008G123500 | XP_002311468 | 14 |
| Potri.009G017300 | XP_002313499 | 15 |

TABLE 1-continued

The list of *Populus trichocarpa* DUF266 and their GenBank accession numbers

| Potri.ID (v3.0) | Genebank_ID | SEQ ID NO |
| --- | --- | --- |
| Potri.010G121800 | XP_002315928 | 16 |
| Potri.010G121900 | XP_002315929 | 17 |
| Potri.010G242900 | XP_002315417 | 18 |
| Potri.011G009500 | XP_002317140 | 19 |
| Potri.015G045400 | XP_002321483 | 20 |
| Potri.015G045500 | XP_002321482 | 21 |
| Potri.018G059100 | XP_002324745 | 22 |
| Potri.018G143900 | XP_002325269 | 23 |
| Potri.T037500 | XP_011002584 | 24 |
| Potri.006G254800 | XP_006382076 | 25 |

To examine the evolutional relationship of DUF266 proteins in different plant species, we performed maximum likelihood phylogenetic analysis. To improve the quality of alignment and phylogenetic tree construction, we excluded those DUF266 proteins with amino acid length <300 or >500. The selected 169 DUF266 proteins were subjected to amino acid sequence alignment and subsequently to the construction of maximum likelihood tree based on the alignment result. Through the construction of maximum likelihood phylogenetic tree based on the MUSCLE alignment result with filtered 169 DUF266 proteins, five clusters were distinctly formed and subsequently these DUF266 proteins are designated as five different groups based on clustering (groups A to E) (FIG. 1). Each cluster contains a set of DUF266 proteins from at least 8 different species except Group E which has no moss or lycophyte DUF266 proteins. All other four groups contain at least one moss DUF266 protein. All three lycophyte DUF266 proteins were associated in three different clades with close relationship with moss DUF266 proteins (FIG. 1). Two clades contain only moss DUF266 proteins (FIG. 1, highlighted in light green). In groups A and C, dicot and monocot nodes were clearly separated (FIG. 1, dicot: highlighted in light blue; monocot: highlighted in light red). In phylogenetic tree, 12 homologs from 9 different plant species shared a cluster together with Potri.011G009500 (Table 2).

TABLE 2

PdDUF266A homologs

| Gene_ID | Genebank ID | SEQ_ID_NO |
| --- | --- | --- |
| LOC_Os01g50040 | XP_015621131 | 26 |
| GRMZM2G152057 | NP_001131182 | 27 |
| Potri.002G227000 | XP_006387659 | 28 |
| Eucgr.K00774 | XP_018720200 | 29 |
| AT1G11940 | NP_172658 | 30 |
| AT1G62305 | NP_683459 | 31 |
| evm_27.TU.AmTr_v1.0_scaffold00106.27 | XP_006838110 | 32 |
| Glyma.09G006600 | KRH36494 | 33 |
| Glyma.15G111000 | XP_006597594 | 34 |
| Eucgr.E03998 | XP_010057900 | 35 |
| GSVIVG01012669001 | XP_002264137 | 36 |
| Potri.T037500 | XP_011002584 | 24 |
| Potri.011G009500 | XP_002317140 | 19 |

Figure 2:
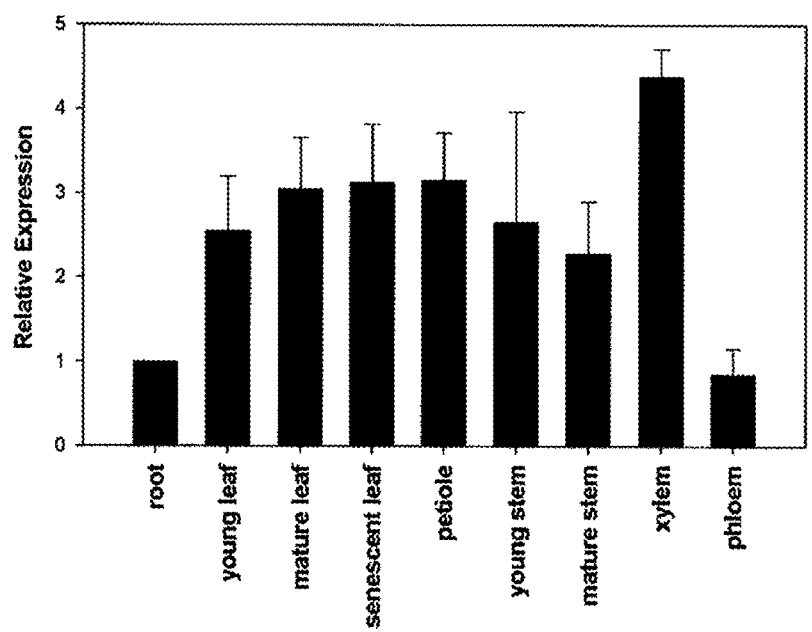
FIG. 2. Expression of PdDUF266A (Potri.011G009500) across *Populus deltoides* tissue types. qRT-PCR analysis of PdDUF266A (Potri.011G009500) expression across various tissues and organs including root, young leaf, mature leaf, young stem (internodes 1 to 3), mature stem (internodes 6 to 8), petiole of mature leaf, phloem (bark of mature stem) and xylem (scrapped stem under bark of mature stem). Relative expression was determined by comparing the PdDUF266A transcript level in other tissues and organs with that in root (set as 1). PdUBCc was used as an internal control. Shown are the mean values of three technical repeats ±S.D.

As an attempt to investigate the function of PdDUF266A, we examined its gene expression patterns across various tissues and organs by qRT-PCR analysis with gene-specific primers. The transcript of PdDUF266A was detected in all tested tissues and organs. PdDUF266A transcript abundance was relatively high in xylem (scraping stem under bark of mature stem) and relatively low in phloem (bark of mature stem, FIG. 2).

Example 3: PdDUF266A Overexpression Leads to Altered Growth Phenotypes in *Populus*

Figures 3A, 3B:
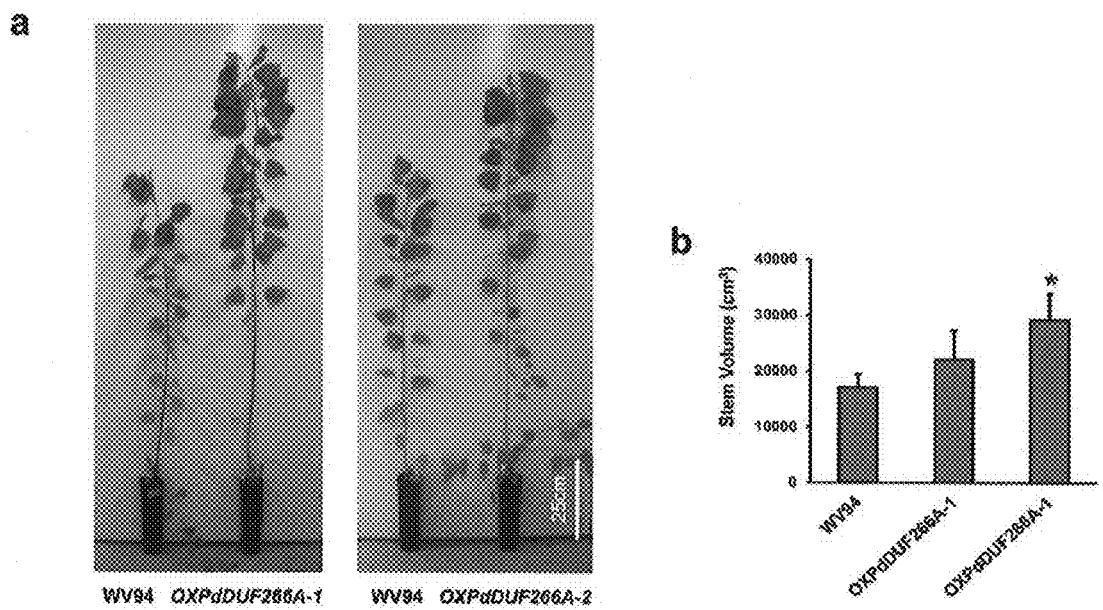
FIG. 3a-3b. Estimated above-ground biomass of transgenic *Populus* samples. a) six-month-old OXPdDUF266A plants grown under greenhouse conditions. b) Estimation of stem volume. Height and diameter were measured in each plant. The volume was estimated by using the $\pi r^2 h$ equation. The bar shows the average value of calculated stem volumes. Error bar displays standard deviation of data set (n=24, 5 and 3 for WV94, OXPdDUF266A-1 and OXPdDUF266A-2, respectively). *Significant compared to the control, p-value ≤0.01.

We observed that *Populus* transgenic plants overexpressing PdDUF266A were constantly larger than control plants under greenhouse conditions. Therefore, we measured the diameter and height and used the stem volume to estimate the biomass amount of OXPdDUF266A plants and compared it with the WV94 control plants. As shown in FIG. 3, the stem volumes of OXPdDUF266A-1 and OXPdDUF266A-2 plants were larger than that of the control plant, indicating that overexpression of PdDUF266A increases biomass production.

Figure 4:
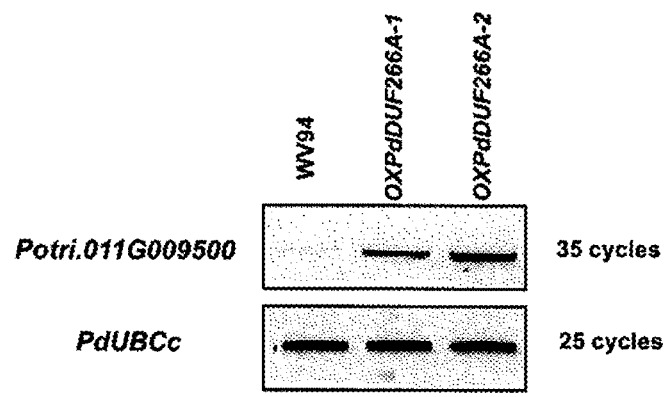
FIG. 4. Relative gene expression of PdDUF266A in transgenic lines overexpressing PdDUF266A (OXPdDUF266A). OXPdDUF266A-1 and PdDUF266A-2 are two independent transgenic lines.

Example 4: Increase in PdDUF266A Transcript Leads to Alteration Total Lignin Quantity To characterize the function of PdDUF266A, *Populus* transgenic plants overexpressing PdDUF266A (OXPdDUF266A) were generated. Among eight transgenic lines, we selected two transgenic lines that had relatively high PdDUF266A gene expression. The transcript level of transgene was examined again in two selected independent *Populus* transgenic lines by RT-PCR with PdDUF266A gene-specific primers. Both OXPdDUF266A lines (OXPdDUF266A-1 and OXPdDUF266A-2) were confirmed to overexpress PdDUF266A. (FIG. 4).

Figures 5A, 5B, 5C:
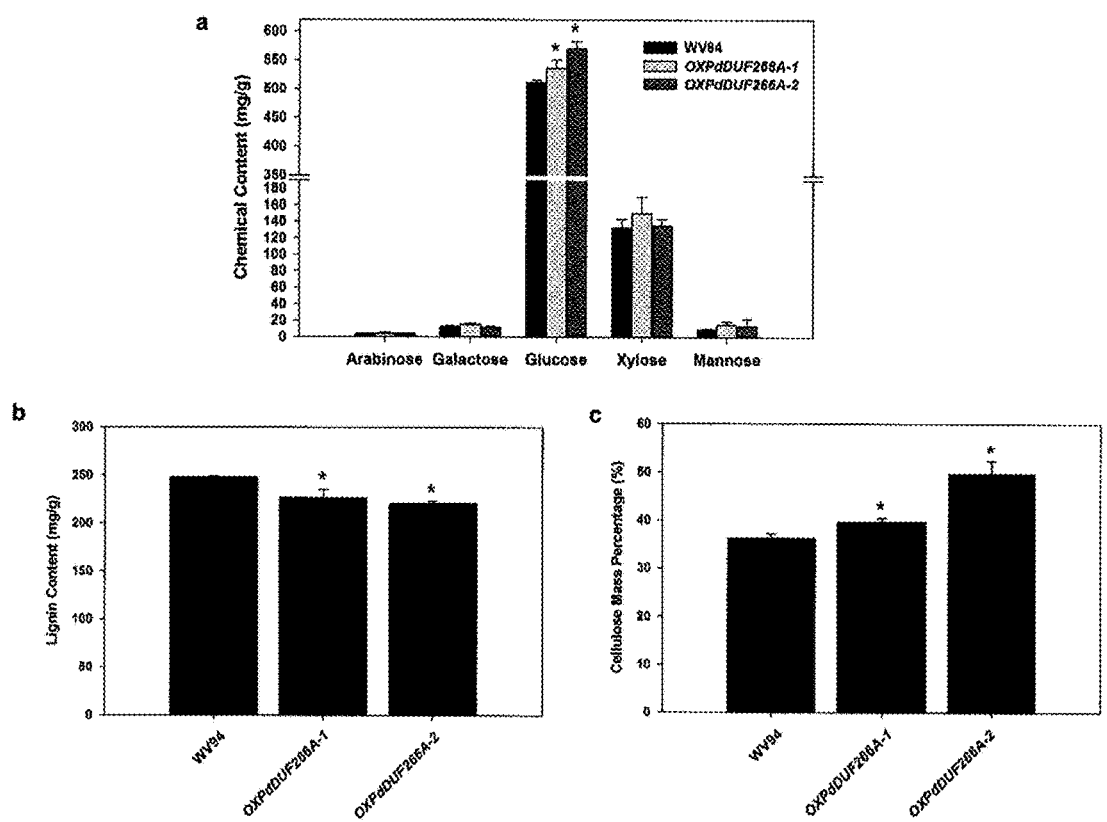
FIG. 5a-5c. Cell wall composition in OXPdDUF266A-1 and OXPdDUF266A-2 transgenic lines. a) Sugar content analysis by using ion chromatography after two step acid treatment. b) Total lignin content by measuring acid soluble/insoluble separation. c) Cellulose content analysis by using Anthrone dye staining. Shown are mean values of three technical repeats from two biological repeats for each transgenic line S.D. Asterisks indicate statistical significance (p<0.01)

We investigated the carbohydrate composition in stem tissues by using ion chromatography after two-step sulfuric acid hydrolysis procedures. OXPdDUF266A-1 and OXPdDUF266A-2 transgenic plants had significantly higher glucose contents (4.8% and 11.4% increase, compared to WV94, respectively) whereas had no significant alteration in the contents of arabinose, galactose, xylose or mannose ($p<0.01$, FIG. 5a). Both transgenic lines had lower lignin content than WV94 (FIG. 5b). Therefore, we focused on the increase of glucose content in OXPdDUF266A transgenic lines to further investigate its impact on saccharification treatment.

To verify whether higher glucose content observed in the OXPdDUF266A transgenic lines was due to higher cellulose content, total cellulose content in stem was estimated by measuring glucose monomer with anthrone staining method. OXPdDUF266A lines had higher cellulose contents (7.6% and 37.1% increase, respectively) compared with that of WV94 (FIG. 5c). This observation supports that increase in glucose content identified by chemical composition analysis is mainly due to increase in cellulose content in OXPdDUF266A lines.

Figures 6A, 6B, 6C:
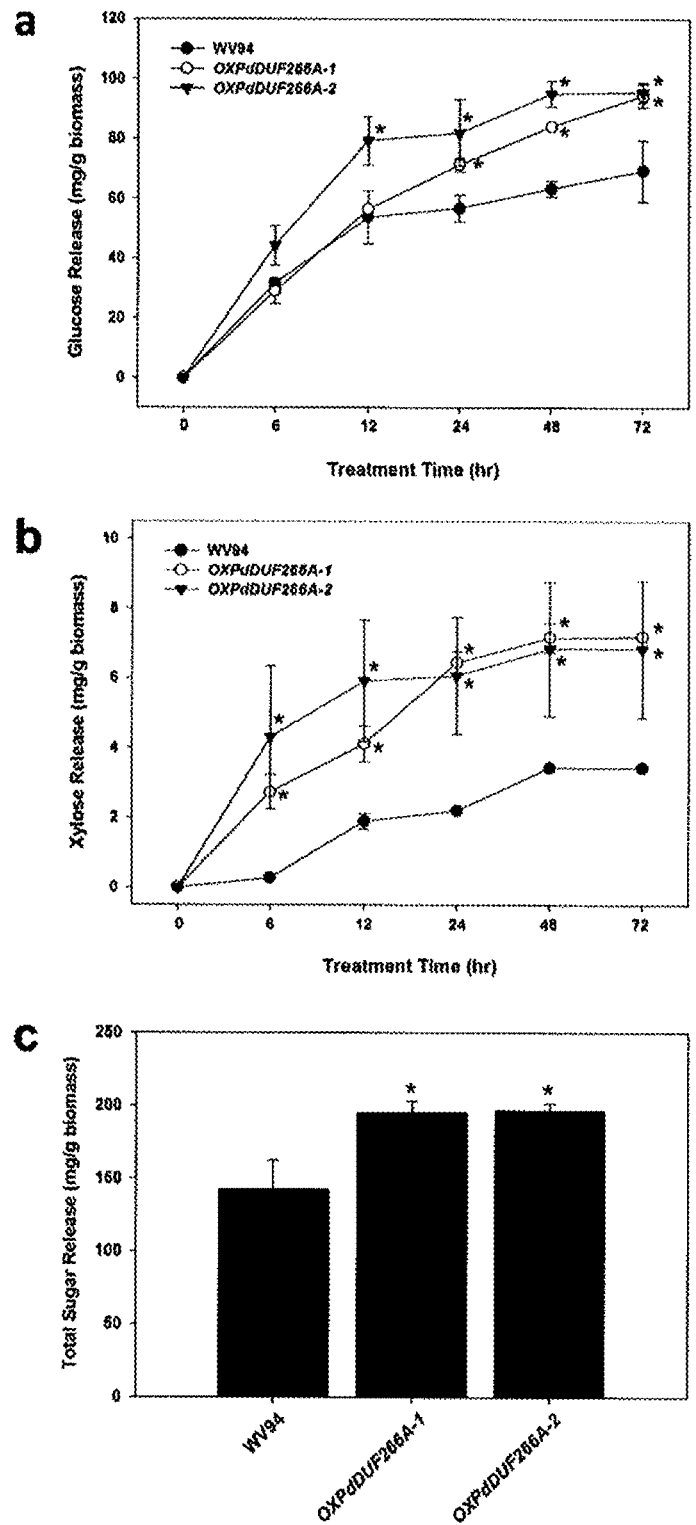
FIGS. 6a-6c. Saccharification efficiency of OXPdDUF266A transgenic plants. Dried *Populus* stem was used for this analysis. a) Glucose release, b) Xylose release. X axis denotes enzymatic hydrolysis time in (a) and (b). c) Total sugar release at 72 h enzymatic hydrolysis. Shown are mean values of two biological replicates ±standard deviation. Asterisks indicate statistical significance (p<0.01).

Example 5: Overexpression of PdDUF266A Transcript Leads to Increased Five and Six Carbon Sugar Release Through cell wall chemical characterization and gene expression analyses, we found that PdDUF266A potentially affects cellulose synthesis. To assess the sugar release performance of the OXPdDUF266A lines, glucose and xylose release during the enzymatic hydrolysis were monitored. At 6 h hydrolysis, the OXPdDUF266A-2 line already had higher glucose release than WV94 (FIG. 6a). More xylose was also released from both OXPdDUF266A lines than WV94 at 6 h hydrolysis (FIG. 6b). At the final time point of 72 h enzymatic hydrolysis, the glucose released from OXPdDUF266A-1 and OXPdDUF266A-2 was 36.2% and 37.9% higher than that from WV94, respectively (FIG. 6a), and the xylose released from the OXPdDUF266A lines was over two folds than that from WV94 (FIG. 6b). The total released sugar at 72 h hydrolysis from OXPdDUF266A-1 and OXPdDUF266A-2 lines were increased by 37.3% and 38.2%, respectively, compared with that from WV94 plant (FIG. 6c). This result indicates that the increase of sugar release could be from both higher cellulose content and increased saccharification rate in the OXPdDUF266A lines.

In summary, the examples herein demonstrate that the overexpression of PdDUF266A resulted in biomass with altered cell wall chemistry leading to the reduction of recalcitrance seen through increased xylose and combined xylose and glucose release. It was observed that the transgenic plants overexpressing PdDUF266A also exhibited an increase in cellulose content and a decrease in lignin content. In addition, those transgenic plants showed an increase in above-ground biomass compared to controls. Therefore, PdDUF266A is involved in higher order interactions of cell wall components. An increase in sugar release was observed in overexpression transgenic lines when samples were subjected to non-pretreatment condition.

What is claimed is:

1. A method for increasing biomass, cellulose content or sugar release in a *Populus* plant, the method comprising:
   (i) transforming *Populus* plants with a recombinant binary vector comprising a DNA expression construct, wherein the DNA expression construct comprises a promoter operably linked to the exogenous coding sequence consisting the nucleic acid sequence as set forth in SEQ ID NO: 37 encoding the protein of SEQ ID NO: 19;
   (ii) expressing said DNA construct in said *Populus* plants; wherein expression of said protein of SEQ ID NO: 19 is increased in said *Populus* plants; and
   (iii) selecting a transformed *Populus* plant from said transformed *Populus* plants of step (ii) which overexpresses said protein of SEQ ID NO: 19 and wherein said selected transformed *Populus* plant exhibits increase in biomass, cellulose content or sugar release as compared to a wild-type untransformed *Populus* plant of the same species lacking said DNA expression construct.

2. The method according to claim 1, wherein said biomass is increased.

3. The method according to claim 1, wherein said cellulose content is increased.

4. The method according to claim 1, wherein said sugar release is increased.

5. The method according to claim 4, wherein the sugar is glucose.

6. The method according to claim 4, wherein the sugar is xylose.

7. A method for decreasing lignin content in a *Populus* plant, the method comprising:
   (i) transforming *Populus* plants with a recombinant binary vector comprising a DNA expression construct, wherein the DNA expression construct comprises a promoter operably linked to the exogenous coding sequence consisting the nucleic acid sequence as set forth in SEQ ID NO: 37 encoding the protein of SEQ ID NO: 19;

(ii) expressing said DNA construct in said *Populus* plants; wherein expression of said protein of SEQ ID NO: 19 is increased in said *Populus* plants; and (iii) selecting a transformed *Populus* plant from said transformed *Populus* plants of step (ii) which overexpresses said protein of SEQ ID NO: 19 and wherein said selected transformed *Populus* plant exhibits decrease in lignin content as compared to a wild-type untransformed *Populus* plant of the same species lacking said DNA expression construct.

* * * * *

SEQUENCE LISTING

```
<160> NUMBER OF SEQ ID NOS: 38

<210> SEQ ID NO 1
<211> LENGTH: 197
<212> TYPE: PRT
<213> ORGANISM: Populus Trichocarpa

<400> SEQUENCE: 1

Met Leu Ser Ser Gln Ile Ile Tyr Ser Phe Ser Leu Leu Ser Val
1               5                   10                  15

Ser Leu Ile Tyr Leu Phe Ser Pro Gln Ile Leu Pro Leu Gln Asn Pro
                20                  25                  30

Gln Asn Leu Pro Leu Asp Glu Leu Tyr Asp Leu Thr Leu Phe Lys Lys
            35                  40                  45

Ala Leu Lys Pro Cys Thr Thr Thr Ser His Leu Ser Thr Arg Asn Pro
        50                  55                  60

Thr Pro Lys Ile Thr Phe Leu Phe Leu Ile Asn Ser Asp Leu Ser Phe
65                  70                  75                  80

Ala Pro Leu Trp Glu His Phe Phe Arg Ser Tyr Asn Asn Leu Tyr Asn
                85                  90                  95

Ile Tyr Val His Ala Asp Pro Phe Ser Lys Val Ser Asn Pro Asp Gly
            100                 105                 110

Ile Phe Lys Asp Gln Phe Ile Pro Gly Lys Lys Thr Glu Met Gly Ser
        115                 120                 125

Pro Ser Leu Ile Ser Ala Glu Lys Arg Leu Leu Ala Arg Ala Ile Leu
    130                 135                 140

Asp Asp Pro Phe Asn Leu His Phe Ala Leu Val Ser Gln His Cys Val
145                 150                 155                 160

Pro Leu His Ser Phe Gln Tyr Met Tyr Asn Thr Leu Phe His Asp Gln
                165                 170                 175

Trp Ser Asp Val Asp Val Pro Cys Ser Ser Ala Gly Phe Gln Arg Gly
            180                 185                 190

Ile Arg Leu Leu Ile
        195

<210> SEQ ID NO 2
<211> LENGTH: 383
<212> TYPE: PRT
<213> ORGANISM: Populus Trichocarpa

<400> SEQUENCE: 2

Met Ala Thr Gln Glu Gly Lys Asp Pro Gly Ile Val Thr Thr Val Arg
1               5                   10                  15

Leu Asn Gln Asn Arg Pro Leu Pro Leu Arg Leu Leu Gln Phe Cys Leu
                20                  25                  30
```

```
Met Phe Leu Val Leu Gly Leu Gly Ile Ser Ile Val Ser Val Asn Met
            35                  40                  45

Ile Arg Phe Phe Gly Val Arg Thr Gly Gly Pro Ala Ala Arg Ser Asn
 50                  55                  60

Ile Ile Phe Pro Cys Phe Glu Glu Ser Asp Ser Ile Glu Lys Trp Ile
 65                  70                  75                  80

Arg Pro Pro Ser Asn Leu Met His Lys Met Asn Asp Thr Glu Leu Phe
                 85                  90                  95

Trp Arg Ala Ser Phe Val Pro Arg Ile Asn Gln Tyr Pro Ile Lys Arg
                100                 105                 110

Val Pro Lys Ile Ala Phe Met Phe Leu Thr Lys Gly Pro Leu Pro Leu
            115                 120                 125

Ala Pro Leu Trp Glu Arg Phe Phe Lys Gly His Glu Gly Leu Tyr Ser
            130                 135                 140

Ile Tyr Val His Ser Leu Pro Ser Tyr Val Ala Asp Leu Thr Arg Phe
145                 150                 155                 160

Ser Val Phe Tyr Lys Arg Gln Ile Pro Ser Gln Val Ala Glu Trp Gly
                165                 170                 175

Met Met Ser Met Cys Asp Ala Glu Arg Arg Leu Leu Ala Asn Ala Leu
            180                 185                 190

Leu Asp Ile Ser Asn Glu Trp Phe Ile Leu Ser Glu Ser Cys Ile
            195                 200                 205

Pro Leu His Asn Phe Gly Ile Ile Tyr Arg Tyr Ile Ser Lys Ser Arg
            210                 215                 220

Tyr Ser Phe Met Gly Val Phe Asp Asp Pro Gly Pro Tyr Gly Arg Gly
225                 230                 235                 240

Arg Tyr Asn Trp Asn Met Gln Pro Glu Val Thr Leu Glu Gln Trp Arg
                245                 250                 255

Lys Gly Ser Gln Trp Phe Glu Val Asp Arg Lys Leu Ala Val Ser Val
            260                 265                 270

Ile Glu Asp Ser Thr Tyr Tyr Pro Lys Phe Lys Asp Phe Cys Arg Pro
            275                 280                 285

Gly Cys Tyr Val Asp Glu His Tyr Phe Pro Thr Met Leu Ser Ile Gln
            290                 295                 300

Phe Pro His Leu Leu Ala Asn Arg Ser Val Thr Trp Thr Asp Trp Ser
305                 310                 315                 320

Arg Gly Gly Ala His Pro Ala Thr Phe Gly Asn Ser Asp Ile Thr Asp
                325                 330                 335

Glu Phe Phe Lys Arg Met Phe Glu Gly Gln Ser Cys Leu Tyr Asn Asn
            340                 345                 350

Gln Pro Asp Asn Val Cys Phe Leu Phe Ala Arg Lys Phe Ser Pro Ser
            355                 360                 365

Ala Leu Glu Pro Leu Leu Asp Leu Ser Pro Lys Val Leu Gly Phe
370                 375                 380

<210> SEQ ID NO 3
<211> LENGTH: 404
<212> TYPE: PRT
<213> ORGANISM: Populus Trichocarpa

<400> SEQUENCE: 3

Met Pro Asn Gln Gln Glu His Pro Lys Ser Gln Arg Asn Ile Ile Ser
 1               5                  10                  15

Leu Met Ala Glu Thr Ser Ser Thr Asn Ser Ile Lys Ile Gly Thr Lys
```

```
            20                  25                  30
Met Phe Ser Thr Gln Phe Val Ile Ile Phe Ser Leu Phe Leu Ser Leu
            35                  40                  45

Pro Ile Leu Phe Leu Leu Ala Pro Arg Ile Phe Pro Ser His Asn Pro
 50                  55                  60

Ser Ile Pro Ile Ser Pro Ser Asp Glu Leu Asp Phe Val Leu Phe
 65                  70                  75                  80

Arg Lys Ala Ile Ala Ser Ala Ser Ala Ser Thr Ser Ala Ser Ala Thr
                     85                  90                  95

Arg Tyr Pro Ser Ala His Ser His Leu Thr Ser Lys Ser Lys Lys Leu
                100                 105                 110

Lys Ile Ala Phe Leu Phe Leu Thr Asn Thr Asp Leu Phe Phe Ala Pro
                115                 120                 125

Leu Trp Glu Gln Phe Phe Lys Ser Ala Asp Lys Asn Leu Phe Asn Ile
           130                  135                 140

Tyr Val His Ala Asp Pro His Ser Asn Val Thr Lys Pro Thr Gly Ile
145                 150                 155                 160

Phe Phe Ser Gln Phe Ile Pro Asp Ala Lys Arg Thr Tyr Arg Ala Ser
                165                 170                 175

Pro Thr Leu Ile Ser Ala Thr Arg Arg Leu Leu Ala Asn Ala Ile Leu
                180                 185                 190

Asp Asp Pro Thr Asn Thr Phe Phe Ala Val Leu Ser Gln Tyr Cys Ile
                195                 200                 205

Pro Leu His Ser Phe Lys Tyr Val Tyr Asn Ser Leu Ile Ser Ser Lys
           210                  215                 220

Ser Phe Asp Leu Ser Ser Pro Glu Ser Asp Pro Glu Ser Thr Lys Tyr
225                 230                 235                 240

Asn Met Lys Ile Gln Tyr Lys Ser Phe Ile Glu Ile Ser Lys Asp
                245                 250                 255

Arg Arg Leu Trp Lys Arg Tyr Val Ser Arg Gly Lys Tyr Ala Met Met
                260                 265                 270

Pro Glu Val Pro Phe Glu Lys Phe Arg Ala Gly Ser Gln Phe Phe Val
           275                  280                 285

Leu Thr Arg Arg His Ala Leu Met Val Ile Glu Asp Arg Leu Trp
           290                  295                 300

Asn Lys Phe Lys Leu Pro Cys Tyr Arg Glu Asp Glu Cys Tyr Pro Glu
305                 310                 315                 320

Glu His Tyr Phe Pro Thr Leu Leu Ser Met Gln Asp Pro Asp Gly Cys
                325                 330                 335

Thr Lys Tyr Thr Leu Thr Lys Val Asn Trp Thr Gly Thr Arg Asn Gly
                340                 345                 350

His Pro Tyr Thr Tyr Lys Ala Ala Glu Ile Ser Pro Val Leu Ile Gln
                355                 360                 365

Glu Leu Arg Gln Ser Asn Tyr Ser Ser Ser Tyr Leu Phe Ala Arg Lys
           370                  375                 380

Phe Glu Pro Ile Cys Leu Asn Pro Leu Met Lys Ile Ala Asp Lys Val
385                 390                 395                 400

Ile Phe Arg Asp

<210> SEQ ID NO 4
<211> LENGTH: 383
<212> TYPE: PRT
<213> ORGANISM: Populus Trichocarpa
```

<400> SEQUENCE: 4

```
Met Lys Gln Arg Lys Ala Thr His Gln Lys Ser Val Tyr Asn Tyr Asn
1               5                   10                  15

Lys Trp Lys Lys Arg Lys Ile Phe Val Met Leu Ser Leu Leu Leu Leu
            20                  25                  30

Leu Gly Phe Cys Leu Val Leu Thr His Asn Ser Thr Thr Thr Asn Thr
        35                  40                  45

Thr Thr Ser Arg Ile Leu Thr Leu Ala Ser Leu Arg Ser His Phe Ile
    50                  55                  60

Val Gln Lys Pro Lys Ile Ala Phe Leu Phe Ile Ala Arg Asn Arg Leu
65                  70                  75                  80

Pro Leu Asp Met Leu Trp Asp Ala Phe Phe Lys Gly Gln Glu Ser Arg
                85                  90                  95

Phe Ser Ile Phe Val His Ser Arg Pro Gly Phe Leu Phe Asn Lys Ala
            100                 105                 110

Asn Thr Arg Ser Glu Tyr Phe Leu Asn Arg Gln Val Asn Asp Ser Ile
        115                 120                 125

Gln Val Asp Trp Gly Gly Ala Ser Met Ile Glu Ala Glu Arg Ile Leu
130                 135                 140

Leu Arg His Ala Leu Val Asp Pro Leu Asn Glu Arg Phe Val Phe Leu
145                 150                 155                 160

Ser Asp Ser Cys Ile Pro Leu Tyr Asn Phe Ser Tyr Thr Tyr Asp Tyr
                165                 170                 175

Ile Met Ser Thr Ser Thr Ser Phe Val Asp Ser Phe Ala Asp Thr Lys
            180                 185                 190

Glu Gly Arg Tyr Asn Pro Lys Met Ala Pro Leu Val Pro Val Tyr Asn
        195                 200                 205

Trp Arg Lys Gly Ser Gln Trp Val Val Leu Thr Arg Lys His Ala Glu
    210                 215                 220

Val Val Val Asn Asp Thr Thr Val Phe Pro Met Phe Gln Gln His Cys
225                 230                 235                 240

Lys Arg Arg Ser Leu Pro Glu Phe Trp Arg Asp His Pro Ile Pro Ala
                245                 250                 255

Asp Thr Ser Met Glu His Asn Cys Ile Pro Asp Glu His Tyr Val Gln
            260                 265                 270

Thr Leu Leu Ala Arg Glu Gly Leu Glu Gly Glu Ile Thr Arg Arg Ser
        275                 280                 285

Leu Thr His Ser Ser Trp Asp Leu Ser Ser Ser Lys Asp Pro Glu Arg
    290                 295                 300

Arg Gly Trp His Pro Val Thr Tyr Lys Phe Ser Asp Ala Thr Pro Thr
305                 310                 315                 320

Leu Ile Gln Ser Ile Lys Asp Ile Asp Asn Ile Tyr Tyr Glu Thr Glu
                325                 330                 335

Tyr Arg Arg Glu Trp Cys Ser Ser Lys Gly Lys Pro Ser Arg Cys Phe
            340                 345                 350

Leu Phe Ala Arg Lys Phe Thr Arg Pro Ala Ala Phe Arg Leu Leu Asn
        355                 360                 365

Met Val Ser Phe Asn Phe Ser Thr Phe Tyr Ser Val Ile Lys Tyr
    370                 375                 380
```

<210> SEQ ID NO 5
<211> LENGTH: 365
<212> TYPE: PRT
<213> ORGANISM: Populus Trichocarpa

<400> SEQUENCE: 5

| | | | | | | | | | | | | | | |
|---|---|---|---|---|---|---|---|---|---|---|---|---|---|---|
| Met | Lys | Ser | Ser | Lys | Pro | Arg | His | Leu | Leu | Trp | Phe | Gly | Phe | Lys | Met |
| 1 | | | | 5 | | | | | 10 | | | | | 15 | |
| Val | Ile | Ala | Leu | Cys | Phe | Leu | Ser | Tyr | Gly | Leu | Phe | Ala | Tyr | Leu | Lys |
| | | | 20 | | | | | 25 | | | | | 30 | | |
| Leu | His | Ser | His | Val | Lys | Leu | Pro | Ser | Leu | His | Pro | Pro | Ala | Phe | His |
| | | 35 | | | | | 40 | | | | | 45 | | | |
| Thr | Ser | Pro | Ser | Ser | Arg | Tyr | His | His | Phe | Glu | Gly | Thr | Pro | Lys | Ile |
| | 50 | | | | | 55 | | | | | 60 | | | | |
| Ala | Phe | Leu | Phe | Leu | Ala | Arg | Arg | Asp | Leu | Pro | Leu | Asp | Phe | Leu | Trp |
| 65 | | | | | 70 | | | | | 75 | | | | | 80 |
| Asp | Ser | Phe | Phe | Lys | Asn | Val | Asp | Ala | Ala | Lys | Phe | Ser | Ile | Tyr | Ile |
| | | | | 85 | | | | | 90 | | | | | 95 | |
| His | Ser | Thr | Pro | Gly | Phe | Val | Phe | Asn | Glu | Thr | Thr | Arg | Ser | Ala |
| | | | 100 | | | | | 105 | | | | | 110 | | |
| Phe | Phe | Tyr | Gly | Gln | Gln | Leu | Asn | Tyr | Ser | Ile | Gln | Val | Ile | Trp | Gly |
| | | | 115 | | | | | 120 | | | | | 125 | | |
| Glu | Ser | Ser | Met | Ile | Glu | Ala | Glu | Lys | Leu | Leu | Leu | Leu | Ala | Ala | Leu |
| | 130 | | | | | 135 | | | | | 140 | | | | |
| His | Asp | Pro | Ala | Asn | Gln | Arg | Phe | Val | Leu | Leu | Ser | Asp | Ser | Cys | Val |
| 145 | | | | | 150 | | | | | 155 | | | | | 160 |
| Pro | Leu | Tyr | Asn | Phe | Ser | Tyr | Leu | Tyr | Ser | Tyr | Leu | Met | Ser | Ser | Ser |
| | | | | 165 | | | | | 170 | | | | | 175 | |
| Lys | Ser | Phe | Val | Asp | Ser | Phe | Ile | Asp | Val | Glu | Glu | Asp | Arg | Tyr | Ser |
| | | | 180 | | | | | 185 | | | | | 190 | | |
| Pro | Lys | Met | Ser | Pro | Val | Ile | Arg | Arg | Asp | Lys | Trp | Arg | Lys | Gly | Ser |
| | | 195 | | | | | 200 | | | | | 205 | | | |
| Gln | Trp | Ile | Thr | Leu | Val | Arg | Arg | His | Ala | Lys | Met | Val | Ala | Glu | Asp |
| | 210 | | | | | 215 | | | | | 220 | | | | |
| Tyr | Phe | Val | Phe | Pro | Ile | Phe | Lys | Glu | Phe | Cys | Lys | Arg | Trp | Pro | Pro |
| 225 | | | | | 230 | | | | | 235 | | | | | 240 |
| Lys | Gly | Val | Asp | Asp | Arg | Lys | Glu | Ile | His | Gln | Ile | Leu | Met | Asn | Gly |
| | | | | 245 | | | | | 250 | | | | | 255 | |
| Leu | Gly | Asp | Glu | Leu | Glu | Arg | Arg | Thr | Leu | Thr | Phe | Thr | Met | Trp | Asn |
| | | | 260 | | | | | 265 | | | | | 270 | | |
| His | Ser | Val | Thr | Lys | Ala | Gln | Thr | Ser | Trp | His | Pro | Val | Thr | Phe | Asp |
| | | 275 | | | | | 280 | | | | | 285 | | | |
| Tyr | Asp | Asp | Ala | Ser | Ala | Lys | Lys | Ile | Lys | Glu | Ile | Lys | Val | Ile | Asn |
| | 290 | | | | | 295 | | | | | 300 | | | | |
| Ser | Ile | Ser | Arg | Lys | Gln | Gly | Asn | Gln | Ser | Glu | Met | Cys | His | Val | Asn |
| 305 | | | | | 310 | | | | | 315 | | | | | 320 |
| Asn | Arg | His | Thr | Pro | Cys | Phe | Leu | Phe | Ala | Arg | Lys | Phe | Thr | Tyr | Arg |
| | | | | 325 | | | | | 330 | | | | | 335 | |
| Ala | Ala | Leu | His | Leu | Leu | Thr | Gln | Asp | Leu | Val | Gly | Ser | Leu | Ile | Leu |
| | | | 340 | | | | | 345 | | | | | 350 | | |
| Leu | His | His | Lys | Thr | Tyr | His | His | Glu | Gln | Leu | His | Tyr |
| | | | 355 | | | | | 360 | | | | | 365 | | |

<210> SEQ ID NO 6
<211> LENGTH: 392
<212> TYPE: PRT
<213> ORGANISM: Populus Trichocarpa

<400> SEQUENCE: 6

```
Met Ala Arg Asn Arg Gly Asp Lys Glu Glu Gly Pro Glu Lys Leu Met
1               5                   10                  15

Gly Leu Leu Lys Leu Val Gln Ile Leu Ser Leu Val Ile Phe Val
            20                  25                  30

Ala Gly Val Ile Leu Gly Leu Ala Thr Ser Ser His Ile Asn Arg Tyr
        35                  40                  45

Phe Thr Ser Gln Ala Gln Leu Phe Leu Thr Asn Asn Ile Ala Ser Ala
    50                  55                  60

Lys Leu Ser Asp Asn Asn Cys Thr Val Val Lys Pro Cys Glu Lys Val
65                  70                  75                  80

Asp Phe Leu Asn Met Glu Arg Phe Val His Pro Asp Asn Val Ile His
                85                  90                  95

Ser Met Thr Asp Asp Gln Val Phe Trp Arg Ala Ser Leu Leu Pro Gln
            100                 105                 110

Lys Lys Gly Tyr Pro Phe Asp Arg Val Pro Lys Val Ala Phe Met Phe
            115                 120                 125

Leu Thr Arg Gly Pro Leu Pro Leu Leu Pro Leu Trp Glu Arg Phe Phe
    130                 135                 140

Arg Gly His Gly Gln Tyr Phe Ser Ile Tyr Val His Thr Pro His Asp
145                 150                 155                 160

Tyr Val Leu Asn Val Ser Ser Asp Ser Pro Phe Tyr Gly Arg Met Ile
                165                 170                 175

Pro Ser Lys Asp Val Glu Trp Gly Ser Val Ser Leu Val Asp Ala Glu
            180                 185                 190

Lys Arg Leu Leu Ala Asn Ala Leu Leu Asp Phe Ser Asn Glu Arg Phe
            195                 200                 205

Val Leu Leu Ser Glu Ser Cys Ile Pro Ile Tyr Asn Phe Pro Thr Val
    210                 215                 220

Tyr Lys Tyr Leu Ile Arg Ser Glu Tyr Ser Phe Val Glu Ser Tyr Asp
225                 230                 235                 240

Glu Pro Thr Arg Tyr Gly Arg Gly Arg Tyr Ser Arg Lys Met Leu Pro
            245                 250                 255

Asp Ile His Leu Tyr Gln Trp Arg Lys Gly Ser Gln Trp Phe Glu Ile
            260                 265                 270

Gln Arg Asp Leu Ala Val Tyr Ile Val Ser Asp Thr Lys Tyr Tyr Thr
    275                 280                 285

Ile Phe Lys Lys Tyr Cys Arg Pro Ala Cys Tyr Pro Asp Glu His Tyr
    290                 295                 300

Ile Pro Thr Tyr Leu Asn Met Phe His Gly Ser Leu Asn Ser Asn Arg
305                 310                 315                 320

Ser Val Thr Trp Val Asp Trp Ser Ile Gly Gly Pro His Pro Ala Arg
                325                 330                 335

Tyr Gly Gly Asn Ile Thr Glu Asp Phe Ile Gln Ser Ile Arg Asn
            340                 345                 350

Asn Gly Thr Gln Cys Ser Tyr Asn Ser Glu Met Thr Ser Val Cys Tyr
            355                 360                 365

Leu Phe Ala Arg Lys Phe Ala Pro Ser Ala Leu Val Pro Leu Leu Ser
    370                 375                 380

Leu Thr Ser Thr Val Met Glu Phe
385                 390

<210> SEQ ID NO 7
<211> LENGTH: 392
```

<212> TYPE: PRT
<213> ORGANISM: Populus Trichocarpa

<400> SEQUENCE: 7

```
Met Ala Arg Asn Arg Gly Asp Lys Glu Glu Gly Pro Glu Lys Leu Met
1               5                   10                  15

Gly Leu Leu Lys Leu Val Gln Ile Leu Ser Leu Val Ile Phe Val
            20                  25                  30

Ala Gly Val Ile Leu Gly Leu Ala Thr Ser Ser His Ile Asn Arg Tyr
        35                  40                  45

Phe Thr Ser Gln Ala Gln Leu Phe Leu Thr Asn Asn Ile Ala Ser Ala
    50                  55                  60

Lys Leu Ser Asp Asn Asn Cys Thr Val Val Lys Pro Cys Glu Lys Val
65              70                  75                  80

Asp Phe Leu Asn Met Glu Arg Phe Val His Pro Asp Asn Val Ile His
                85                  90                  95

Ser Met Thr Asp Asp Gln Val Phe Trp Arg Ala Ser Leu Leu Pro Gln
            100                 105                 110

Lys Lys Gly Tyr Pro Phe Asp Arg Val Pro Lys Val Ala Phe Met Phe
        115                 120                 125

Leu Thr Arg Gly Pro Leu Pro Leu Leu Pro Leu Trp Glu Arg Phe Phe
    130                 135                 140

Arg Gly His Gly Gln Tyr Phe Ser Ile Tyr Val His Thr Pro His Asp
145                 150                 155                 160

Tyr Val Leu Asn Val Ser Ser Asp Ser Pro Phe Tyr Gly Arg Met Ile
                165                 170                 175

Pro Ser Lys Asp Val Glu Trp Gly Ser Val Ser Leu Val Asp Ala Glu
            180                 185                 190

Lys Arg Leu Leu Ala Asn Ala Leu Leu Asp Phe Ser Asn Glu Arg Phe
        195                 200                 205

Val Leu Leu Ser Glu Ser Cys Ile Pro Ile Tyr Asn Phe Pro Thr Val
    210                 215                 220

Tyr Lys Tyr Leu Ile Arg Ser Glu Tyr Ser Phe Val Glu Ser Tyr Asp
225                 230                 235                 240

Glu Pro Thr Arg Tyr Gly Arg Gly Arg Tyr Ser Arg Lys Met Leu Pro
                245                 250                 255

Asp Ile His Leu Tyr Gln Trp Arg Lys Gly Ser Gln Trp Phe Glu Ile
            260                 265                 270

Gln Arg Asp Leu Ala Val Tyr Ile Val Ser Asp Thr Lys Tyr Tyr Thr
        275                 280                 285

Ile Phe Lys Lys Tyr Cys Arg Pro Ala Cys Tyr Pro Asp Glu His Tyr
    290                 295                 300

Ile Pro Thr Tyr Leu Asn Met Phe His Gly Ser Leu Asn Ser Asn Arg
305                 310                 315                 320

Ser Val Thr Trp Val Asp Trp Ser Ile Gly Gly Pro His Pro Ala Arg
                325                 330                 335

Tyr Gly Gly Gly Asn Ile Thr Glu Asp Phe Ile Gln Ser Ile Arg Asn
            340                 345                 350

Asn Gly Thr Gln Cys Ser Tyr Asn Ser Glu Met Thr Ser Val Cys Tyr
        355                 360                 365

Leu Phe Ala Arg Lys Phe Ala Pro Ser Ala Leu Val Pro Leu Leu Ser
    370                 375                 380

Leu Thr Ser Thr Val Met Glu Phe
385                 390
```

```
<210> SEQ ID NO 8
<211> LENGTH: 159
<212> TYPE: PRT
<213> ORGANISM: Populus Trichocarpa

<400> SEQUENCE: 8

Met Ala Phe Val Phe Phe Thr Arg Gly Ser Val Pro Met Leu Pro Leu
1               5                   10                  15

Trp Glu Arg Phe Arg Gly His Glu Lys Leu Tyr Ser Ile Tyr Val
                20                  25                  30

His Ala His Pro Lys Tyr Arg Ile Lys Ala Ser Lys Asp Ser Pro Phe
            35                  40                  45

His Gly Tyr Met Leu Ala Ile Asp Ala Lys Lys Arg Leu Leu Val Asn
        50                  55                  60

Ala Leu Leu Asp Phe Ser Asn Glu Trp Phe Pro Phe Leu Ser Glu Ser
65                  70                  75                  80

Cys Ile Pro Val Tyr Lys Phe His His Val Cys Ile Ser His Thr
                85                  90                  95

Ile Lys Thr Gln Leu Cys Gly Val Leu Tyr Glu Leu Ser Ser Asp Gly
            100                 105                 110

Arg Gly Arg Tyr Phe His Gln Ile Leu Pro Lys Ile Gln Leu His Gln
        115                 120                 125

Trp Arg Lys Gly Ser Gln Trp Leu Ala Ile Gln Arg Asp Leu Ala Ile
    130                 135                 140

Tyr Ile Val Tyr Glu Thr Lys Cys His Val Val Phe Lys Lys His
145                 150                 155

<210> SEQ ID NO 9
<211> LENGTH: 299
<212> TYPE: PRT
<213> ORGANISM: Populus Trichocarpa

<400> SEQUENCE: 9

Met His Asn Met Ser Asp Glu Glu Leu Leu Arg Arg Ala Ser Met Val
1               5                   10                  15

Pro Ile Val Gln Glu Ser Ala Gln Lys Gln Ala Pro Lys Val Ala Phe
                20                  25                  30

Met Phe Leu Thr Asn Gly Pro Leu Pro Leu Ser Leu Leu Trp Glu Lys
            35                  40                  45

Phe Phe Glu Gly His Glu Gly Leu Tyr Ser Ile Tyr Val His Pro His
        50                  55                  60

Pro Ser Tyr Asn Asp Ser Trp Pro Arg Ser Ser Val Phe Phe Gly Arg
65                  70                  75                  80

Arg Ile Pro Ser Gln Ala Val Tyr Trp Gly Thr Gly Thr Met Ile Asp
                85                  90                  95

Ala Glu Arg Arg Leu Leu Ala Asn Ala Leu Leu Asp Ser Ser Asn Gln
            100                 105                 110

Arg Phe Val Leu Leu Ser Glu Ser Cys Ile Pro Leu Phe Asn Phe Lys
        115                 120                 125

Thr Thr Tyr Asp His Leu Met Asn Ser Asn Ile Ser Phe Leu Gly Ser
    130                 135                 140

Phe Asp Asp Pro Arg Lys Pro Gly Arg Gly Arg Tyr Asn Pro Arg Met
145                 150                 155                 160

Trp Pro Ala Ile Asn Ile Thr Asp Trp Arg Lys Gly Ser Gln Trp Phe
                165                 170                 175
```

```
Glu Val His Arg Asp Ile Ala Val His Ile Ile Ser Asp Gln Lys Tyr
            180                 185                 190

Tyr Gln Val Phe Gln Glu His Cys His Pro Pro Cys Tyr Met Asp Glu
        195                 200                 205

His Tyr Phe Pro Thr Leu Val Asn Ile Leu Tyr Pro Glu Leu Asn Ser
    210                 215                 220

Asn Arg Ser Ile Thr Trp Val Asp Trp Ser Arg Gly Gly Pro His Pro
225                 230                 235                 240

Gly Lys Phe Arg Trp Ala Asp Ile Thr Asp Glu Phe Leu Asn Gln Ile
                245                 250                 255

Arg His Gly Ser Glu Cys Val Tyr Asn Gly Asn Thr Thr Ser Met Cys
            260                 265                 270

Tyr Leu Phe Ala Arg Lys Phe Leu Pro Gln Thr Leu Glu Pro Leu Leu
        275                 280                 285

Arg Ile Ala Pro Leu Leu His Val Phe Asp Pro
    290                 295

<210> SEQ ID NO 10
<211> LENGTH: 392
<212> TYPE: PRT
<213> ORGANISM: Populus Trichocarpa

<400> SEQUENCE: 10

Met Ala Arg Asn Arg Trp Asp Arg Glu Asp Ala Pro Glu Lys His Ile
1               5                   10                  15

Gly Leu Leu Gln Leu Val Gln Met Leu Ser Leu Leu Val Ile Phe Val
            20                  25                  30

Ala Gly Ile Ile Ile Gly Ile Ala Thr Ser Pro His Ile Asn Arg Tyr
        35                  40                  45

Phe Asp Ser Leu Ala Gln Leu Thr Phe Thr Asn Asn Ile Ala Ser Pro
    50                  55                  60

Lys Ile Ser Asp Asp Asn Cys Thr Ile Leu Arg Thr Cys Glu Lys Val
65                  70                  75                  80

Asp Cys Leu Thr Met Glu Gly Phe Val His Pro Asp Asn Leu Thr His
                85                  90                  95

Ser Met Thr Asp Asp Glu Val Leu Trp Arg Ala Ser Met Leu Pro Tyr
            100                 105                 110

Lys Lys Gly Tyr Pro Phe Asp Arg Val Pro Lys Val Ala Phe Met Phe
        115                 120                 125

Leu Thr Arg Gly Pro Leu Pro Leu Leu Pro Leu Trp Glu Arg Phe Phe
    130                 135                 140

Arg Gly His Ala Gly Tyr Phe Ser Ile Tyr Val His Thr Pro Glu Asp
145                 150                 155                 160

Tyr Glu Leu Asn Val Ser Thr Asp Ser Pro Phe Tyr Gly Arg Lys Ile
                165                 170                 175

Pro Ser Lys Asp Val Glu Trp Gly Ser Ile Ser Met Val Asp Ala Glu
            180                 185                 190

Lys Arg Leu Leu Ala Asn Ala Leu Leu Asp Phe Ser Asn Glu Arg Phe
        195                 200                 205

Val Leu Leu Ser Glu Ser Cys Ile Pro Ile Tyr Lys Phe Ser Ile Val
    210                 215                 220

Tyr Lys Tyr Leu Ile Arg Ser Lys His Ser Phe Val Glu Ser Tyr Asp
225                 230                 235                 240

Ala Pro Thr Arg Tyr Ala Arg Gly Arg Tyr Asn Gln Lys Met Leu Pro
```

```
                    245                 250                 255
Asp Ile His Leu Tyr Gln Trp Arg Lys Gly Ser Gln Trp Phe Glu Ile
            260                 265                 270

Gln Arg Asp Leu Ala Val Tyr Leu Val Ser Asp Thr Lys Tyr His Thr
            275                 280                 285

Ile Phe Lys Lys Tyr Cys Arg Pro Ala Cys Tyr Pro Asp Glu His Tyr
            290                 295                 300

Ile Pro Thr Tyr Leu Asn Met Phe His Gly Ser Leu Asn Ala Asn Arg
305                 310                 315                 320

Thr Val Thr Trp Val Asp Trp Ser Ile Val Ala Pro His Pro Pro Thr
                325                 330                 335

Tyr Asp Gly Ile Asp Val Thr Glu Gly Phe Ile Gln Ser Ile Arg Asn
            340                 345                 350

Lys Gly Asn Gln Cys Ser Tyr Asn Ser Glu Met Thr Ser Val Cys Tyr
            355                 360                 365

Leu Phe Ala Arg Lys Phe Ala Pro Ser Ala Leu Val Pro Leu Leu Asn
            370                 375                 380

Leu Thr Ser Thr Val Met Gly Phe
385                 390

<210> SEQ ID NO 11
<211> LENGTH: 392
<212> TYPE: PRT
<213> ORGANISM: Populus Trichocarpa

<400> SEQUENCE: 11

Met Lys Thr Pro Gln Leu Trp Arg Leu Gly Met Gly Asp Val Gln Ile
1               5                   10                  15

Leu His Gly Ala Arg His Arg Pro Pro Leu Lys Arg Pro Met Trp Ile
            20                  25                  30

Ile Ile Leu Val Ser Met Val Ser Leu Phe Leu Val Cys Ala Tyr Ile
            35                  40                  45

Tyr Pro Pro Gln Ser Ser Ser Ala Cys Tyr Val Phe Ser Ser Arg Gly
50                  55                  60

Cys Lys Val Leu Thr Asp Trp Leu Pro Ala Pro Thr Arg Glu Phe
65                  70                  75                  80

Thr Asp Glu Glu Ile Ala Ser Arg Ile Val Val Arg Glu Ile Leu Asn
            85                  90                  95

Thr Pro Ser Ile Pro Thr Lys Lys Ala Lys Ile Ala Phe Met Phe Leu
            100                 105                 110

Thr Thr Ser Leu Leu Pro Phe Glu Lys Leu Trp Asp Lys Phe Phe Ser
            115                 120                 125

Gly His Glu Asp Arg Phe Ser Val Tyr Val His Ala Ser Lys Glu Lys
            130                 135                 140

Pro Val His Val Ser Arg Tyr Phe Val Asp Arg Asp Val Arg Ser Asp
145                 150                 155                 160

Gln Val Ile Trp Gly Gln Ile Ser Met Ile Asp Ala Glu Arg Arg Leu
                165                 170                 175

Leu Ala Asn Ala Leu Gly Asp Pro Asp Asn Gln His Phe Val Leu Leu
            180                 185                 190

Ser Asp Ser Cys Val Pro Leu Tyr Lys Phe Asp His Ile Tyr Asn Tyr
            195                 200                 205

Leu Met Tyr Ser Asn Met Ser Tyr Leu Asp Cys Phe Tyr Asp Pro Gly
            210                 215                 220
```

```
Pro His Gly Asn Gly Arg Tyr Ser Glu His Met Leu Pro Glu Ile Glu
225                 230                 235                 240

Leu Lys Asp Phe Arg Lys Gly Ala Gln Trp Phe Ser Met Lys Arg Gln
            245                 250                 255

His Ala Val Ile Val Met Ala Asp Ser Leu Tyr Tyr Thr Lys Phe Arg
        260                 265                 270

Asp Tyr Cys Lys Pro Gly Leu Glu Gly Lys Asn Cys Ile Ala Asp Glu
    275                 280                 285

His Tyr Leu Pro Thr Phe Phe His Ile Val Asp Pro Gly Gly Ile Ala
290                 295                 300

Asn Trp Ser Val Thr His Val Asp Trp Ser Glu Arg Lys Trp His Pro
305                 310                 315                 320

Lys Leu Tyr Arg Thr Gln Asp Val Thr Ser Glu Leu Leu Lys Asn Ile
            325                 330                 335

Thr Ser Ile Asp Leu Ser Ile His Val Thr Ser Asp Glu Lys Arg Asp
        340                 345                 350

Val Gln Val Gln Pro Cys Leu Trp Asn Gly Thr Thr Arg Pro Cys Tyr
    355                 360                 365

Leu Phe Ala Arg Lys Phe His Pro Glu Thr Thr Asp Asn Leu Leu Lys
370                 375                 380

Leu Phe Ser Asn Tyr Thr Ser Leu
385                 390

<210> SEQ ID NO 12
<211> LENGTH: 385
<212> TYPE: PRT
<213> ORGANISM: Populus Trichocarpa

<400> SEQUENCE: 12

Met Gln Ser Arg Val Val Pro Leu Glu Glu Gly Lys Asp Pro Ala Val
1               5                   10                  15

Ser Ile Lys Ala Ser Gln Ser Lys Pro Phe Pro Ile Arg Leu Leu Gln
            20                  25                  30

Leu Phe Leu Leu Phe Leu Ala Leu Cys Met Ala Phe Ser Ile Ile Ser
        35                  40                  45

Met Tyr Thr Ile Lys Arg Phe Gly Val Gln Thr Ala Arg Thr Thr Val
    50                  55                  60

Lys Pro Ala Phe Glu Pro Cys Phe Asp Glu Pro Asp Thr Leu Asp Arg
65                  70                  75                  80

Trp Ile Arg Pro Pro Ser Asn Leu Leu His Lys Met Ser Asp Lys Glu
            85                  90                  95

Leu Phe Trp Arg Ala Ser Phe Val Pro Gly Ile Lys Lys Tyr Pro Phe
        100                 105                 110

Lys Arg Ile Pro Lys Ile Ala Phe Met Phe Leu Thr Lys Gly Pro Leu
    115                 120                 125

Pro Leu Ala Pro Leu Trp Glu Arg Phe Leu Lys Gly His Glu Gly Leu
130                 135                 140

Tyr Ser Val Tyr Ile His Pro Leu Pro Thr Phe Glu Ala Lys Phe Pro
145                 150                 155                 160

Ser Ser Ser Val Phe His Arg Arg Gln Ile Pro Ser Gln Val Ala Glu
            165                 170                 175

Trp Gly Arg Met Ser Met Cys Asp Ala Glu Arg Arg Leu Leu Ala Asn
        180                 185                 190

Ala Leu Leu Asp Ile Ser Asn Glu Arg Phe Val Leu Val Ser Glu Ser
    195                 200                 205
```

```
Cys Ile Pro Leu Tyr Asn Phe Ser Val Ile Tyr Asp Tyr Met Met Arg
    210                 215                 220

Ser Lys Tyr Ser Phe Ile Gly Ala Phe Asp Asp His Gly Pro Tyr Gly
225                 230                 235                 240

Arg Gly Arg Tyr Asn Glu Asn Met Ala Pro Glu Val Asn Ile Thr Gln
                245                 250                 255

Trp Arg Lys Gly Ser Gln Trp Phe Glu Ile Asn Arg Lys Leu Ala Val
            260                 265                 270

Asn Val Val Glu Asp Ala Arg Tyr Tyr Pro Lys Phe Glu Glu Phe Cys
        275                 280                 285

Lys Pro Ser Cys Tyr Val Asp Glu His Tyr Phe Pro Thr Met Leu Thr
    290                 295                 300

Ile Glu Ala Ala Pro Leu Leu Ala Asn Arg Thr Leu Thr Trp Val Asp
305                 310                 315                 320

Trp Ser Arg Gly Gly Ala His Pro Ala Thr Phe Gly Arg Ala Asp Ile
                325                 330                 335

Thr Lys Glu Phe Phe Lys Lys Ile Arg Glu Asp Thr His Cys Val Tyr
            340                 345                 350

Asn Asn Gln Ser Ser Pro Val Cys Phe Leu Phe Ala Arg Lys Phe Ala
        355                 360                 365

Pro Ser Ala Leu Glu Pro Leu Leu Gln Val Ser Gln Asn Val Leu Gly
    370                 375                 380

Phe
385

<210> SEQ ID NO 13
<211> LENGTH: 345
<212> TYPE: PRT
<213> ORGANISM: Populus Trichocarpa

<400> SEQUENCE: 13

Met Leu Ser Ser Pro Ile Ile Tyr Ser Phe Ser Leu Leu Leu Ser Phe
1               5                   10                  15

Ser Leu Ile Tyr Leu Phe Ser Pro Gln Ile Leu Pro Leu Gln Asn Pro
            20                  25                  30

Gln Asn Leu Pro Leu Asp Glu Leu Glu Asp Leu Thr Leu Phe Lys Lys
        35                  40                  45

Ala Leu Lys Pro Cys Thr Thr Thr Ser His Leu Ser Thr Arg Asn Pro
    50                  55                  60

Thr Pro Lys Ile Ala Phe Leu Phe Leu Thr Asn Ser Asp Leu Ser Phe
65                  70                  75                  80

Ala Pro Leu Trp Glu Arg Phe Phe Arg Gly Tyr Ser Asn Leu Tyr Asn
                85                  90                  95

Ile Tyr Val His Ala Asp Pro Phe Ser Lys Val Ser Asn Pro Asp Gly
            100                 105                 110

Ile Phe Lys Asp Gln Phe Ile Pro Gly Lys Lys Thr Glu Arg Gly Ser
        115                 120                 125

Pro Ser Leu Ile Ser Ala Glu Lys Arg Leu Leu Ala Arg Ala Ile Leu
    130                 135                 140

Asp Asp Pro Phe Asn Leu Tyr Phe Ala Leu Val Ser Gln His Cys Val
145                 150                 155                 160

Pro Leu His Ser Phe Gln Tyr Met Tyr Asn Thr Leu Phe Gly His Asn
                165                 170                 175

Ile Leu Glu Ala Phe Ala Ala Gln Ser His His Gln Ser Phe Ile Glu
```

```
            180             185             190
Ile Leu Ser Gln Asp Pro Asn Leu Pro Asp Arg Tyr Asn Ala Arg Gly
            195             200             205

Glu Asn Ile Met Leu Pro Glu Ile Pro Phe Glu Lys Phe Arg Val Gly
210             215             220

Ser Gln Phe Phe Val Leu Ala Lys Arg His Ala Phe Leu Val Leu Lys
225             230             235             240

Asp Arg Lys Leu Trp Arg Lys Phe Lys Leu Pro Cys Leu Asn Ile Glu
            245             250             255

Ser Cys Tyr Pro Glu Glu His Tyr Phe Pro Thr Leu Leu Ser Met Lys
            260             265             270

Asp Pro Arg Gly Cys Ser Gln Tyr Thr Leu Thr Asn Val Asn Trp Thr
            275             280             285

Asp Cys Phe Asp Ala His Pro His Leu Tyr Gln Ala Glu Glu Val Ser
            290             295             300

Pro Asn Leu Val His Arg Leu Arg Leu Ser Asn Ser Ser Asp Ser Tyr
305             310             315             320

Phe Phe Ala Arg Lys Phe Ala Pro Asp Cys Leu Lys Pro Leu Met Glu
            325             330             335

Ile Ala Asp Asp Val Ile Phe Lys Asp
            340             345

<210> SEQ ID NO 14
<211> LENGTH: 391
<212> TYPE: PRT
<213> ORGANISM: Populus Trichocarpa

<400> SEQUENCE: 14

Met Lys Gly Gln Lys Gln Asn Leu Pro Thr Thr Ser Thr Lys Leu Phe
1               5               10              15

Asn Ala Gln Leu Gln Leu Ile Asn Val Leu Ser Phe Leu Phe Leu Phe
            20              25              30

Gly Cys Gly Leu Val Thr Gly Val Val Leu Ser Ser Tyr Leu Lys His
            35              40              45

Val Ser Cys Asn Leu His Val Ser Gln Phe Ser Val Ser Thr Thr Thr
        50              55              60

Thr Thr Thr Val Pro Leu Ala Thr Leu Pro Ala Phe Lys Leu Pro Arg
65              70              75              80

Val Gly Leu Lys Glu His Leu Lys Val Pro Asp Val Lys His Asp Met
            85              90              95

Asp Glu Lys Glu Leu Leu Trp Arg Ala Ser Met Thr Pro Arg Ile Arg
            100             105             110

Glu Tyr Pro Phe Asp Arg Val Pro Lys Val Ala Phe Met Phe Leu Thr
            115             120             125

Lys Gly Pro Val Leu Met Ala Pro Leu Trp Glu Arg Phe Phe Gln Gly
            130             135             140

His Glu Gly Leu Tyr Ser Ile Tyr Val His Ser Ser Pro Ser Tyr Asn
145             150             155             160

Glu Ser Glu Pro Glu Ser Pro Val Phe His Gly Arg Arg Ile Pro Ser
            165             170             175

Lys Asp Val Gln Trp Gly Asn Thr Asn Ile Ile Glu Ala Glu Arg Arg
            180             185             190

Leu Leu Ala Asn Ala Leu Leu Asp Ile Ser Asn Gln Arg Phe Val Leu
            195             200             205
```

```
Leu Ser Glu Ser Cys Ile Pro Ile Phe Asp Phe Ser Thr Val Tyr Thr
    210                 215                 220

Tyr Leu Met Asn Ser Thr Lys Asn His Val Asp Ser Tyr Val Leu Asp
225                 230                 235                 240

Gly Pro Val Gly Asn Gly Arg Tyr Asn Pro Arg Met Arg Pro Val Ile
                245                 250                 255

Lys Ile Glu His Trp Arg Lys Gly Ser Gln Trp Phe Glu Met Asp Arg
            260                 265                 270

Asp Leu Ala Ile Glu Val Val Ser Asp Gln Tyr Phe Pro Val Phe
            275                 280                 285

Gln Lys Tyr Cys Lys Gly His Cys Tyr Ala Asp Glu His Tyr Leu Pro
    290                 295                 300

Thr Phe Val Ser Met Lys His Ser Glu Arg Asn Ser Asn Arg Ser Leu
305                 310                 315                 320

Thr Trp Val Asp Trp Ser Arg Gly Gly Ala His Pro Ala Lys Phe Leu
                325                 330                 335

Ser Arg Glu Val Thr Ile Glu Phe Leu Glu Arg Met Arg Ser Gly Ser
            340                 345                 350

Lys Cys Val Tyr Asn Gly Asn Ser Thr Asn Thr Cys Phe Leu Phe Ala
    355                 360                 365

Arg Lys Phe Trp Pro Ala Leu Glu Arg Leu Leu Arg Phe Ala Pro
370                 375                 380

Lys Val Met His Phe Asn Ser
385                 390

<210> SEQ ID NO 15
<211> LENGTH: 388
<212> TYPE: PRT
<213> ORGANISM: Populus Trichocarpa

<400> SEQUENCE: 15

Met Pro Glu Thr Ser Thr Asn Cys Pro Asn Ser Ile Lys Ile Gly
1               5                   10                  15

Pro Val Met Phe Thr Thr Gln Phe Leu Leu Val Phe Ser Leu Leu Leu
                20                  25                  30

Ser Leu Pro Ile Leu Phe Leu Leu Ala Pro Arg Ile Phe Pro Pro His
            35                  40                  45

Asn Pro Ser Ile Pro Ile Ser Pro Ser Asp Glu Gln Asp Asp Leu Tyr
        50                  55                  60

Leu Phe Arg Lys Ala Ala Ala Ala Ala Ser Ser Phe Val Thr
65                  70                  75                  80

His Tyr Pro Ser Ala His Thr His Phe Thr Ser Lys Ser Lys Leu
                85                  90                  95

Lys Ile Ala Phe Leu Phe Leu Thr Asn Thr Asp Leu Phe Ala Pro
            100                 105                 110

Leu Trp Glu Gln Phe Phe Lys Ser Ala Asp Lys Asn Leu Phe Asn Ile
        115                 120                 125

Tyr Val His Ala Asp Pro Tyr Ser Asn Val Thr Lys Ala Lys Gly Val
    130                 135                 140

Phe Ser Ser Gln Phe Ile Pro Asn Ala Lys Arg Thr Tyr Arg Ala Ser
145                 150                 155                 160

Pro Thr Leu Ile Ser Ala Thr Arg Arg Leu Leu Ala Thr Ala Ile Leu
                165                 170                 175

Asp Asp Pro Thr Asn Thr Phe Phe Ala Val Leu Ser Gln Tyr Cys Ile
            180                 185                 190
```

```
Pro Leu His Ser Phe Lys Tyr Val Tyr Asp Ser Leu Ile Ser Ser Lys
        195                 200                 205

Ser Phe Asp Phe Ser Ser Glu Ser Gly Pro Glu Ser Thr Gln Tyr
    210                 215                 220

Asn Val Lys Ile Glu Tyr Lys Ser Phe Val Glu Ile Ser Lys Glu
225                 230                 235                 240

Arg Arg Leu Trp Lys Arg Tyr Val Ala Arg Gly Arg Tyr Ser Met Met
                245                 250                 255

Pro Glu Val Pro Phe Glu Lys Phe Arg Gly Gly Ser Gln Phe Phe Val
                260                 265                 270

Ile Thr Arg Arg His Ala Leu Met Val Ile Glu Asp Arg Arg Leu Trp
            275                 280                 285

Asn Lys Phe Lys Gln Pro Cys Asn Arg Glu Asp Glu Cys Tyr Pro Glu
            290                 295                 300

Glu His Tyr Phe Pro Thr Leu Leu Ser Met Gln Asp Pro Lys Gly Cys
305                 310                 315                 320

Thr Lys Tyr Thr Leu Thr Arg Val Asn Trp Thr Gly Thr Arg Asn Gly
                325                 330                 335

His Pro Tyr Thr Tyr Lys Ala Ser Glu Ile Ser Pro Val Leu Ile Gln
                340                 345                 350

Glu Leu Arg Lys Ser Asn Tyr Ser Ser Tyr Leu Phe Ala Arg Lys
            355                 360                 365

Phe Glu Pro Asn Cys Leu Lys Pro Leu Met Lys Ile Ala Asp Glu Val
            370                 375                 380

Ile Phe Gln Asp
385

<210> SEQ ID NO 16
<211> LENGTH: 389
<212> TYPE: PRT
<213> ORGANISM: Populus Trichocarpa

<400> SEQUENCE: 16

Met Lys Gly Gln Thr Gln Asn Gln Asn Leu Val Thr Ala Phe Thr Lys
1               5                   10                  15

Leu Phe Asn Ala Gln Leu Gln Leu Ile Asn Val Leu Ser Leu Phe Phe
                20                  25                  30

Leu Phe Gly Cys Gly Leu Ala Thr Gly Val Ile Leu Ser Ser Tyr Leu
            35                  40                  45

Asn Asn Ile Ser Phe Asn Leu Gln Val Ser His Phe Ser Phe Ser Thr
50                  55                  60

Thr Thr Thr Thr Ala Ser Pro Thr Phe Lys Leu Pro Pro Arg Val Gly
65                  70                  75                  80

Leu Lys Glu Tyr Leu Lys Val Pro Asp Val Lys His Asp Met Asp Glu
                85                  90                  95

Lys Glu Leu Leu Trp Arg Ala Ser Val Thr Pro Asn Ile Arg Glu Phe
            100                 105                 110

Pro Phe Asp Arg Val Pro Lys Val Ala Phe Met Phe Leu Thr Lys Gly
            115                 120                 125

Pro Val Leu Met Ala Pro Leu Trp Glu Lys Phe Phe Lys Gly His Asp
            130                 135                 140

Gly Leu Tyr Ser Ile Tyr Val His Ser Pro Ser Tyr Asn Glu Ser
145                 150                 155                 160

Glu Pro Glu Ser Pro Val Phe His Gly Arg Arg Ile Pro Ser Lys Val
```

```
            165                 170                 175
Val Gln Trp Gly Asn Ala Asn Met Ile Glu Ala Glu Arg Arg Leu Leu
        180                 185                 190

Ala Asn Ala Leu Leu Asp Ile Ala Asn Gln Arg Phe Val Leu Leu Ser
        195                 200                 205

Glu Ser Cys Ile Pro Leu Phe Asn Phe Ser Thr Val Tyr Thr Tyr Leu
210                 215                 220

Met Asn Ser Thr Lys Ser His Val Glu Ser Tyr Val Leu Glu Gly Pro
225                 230                 235                 240

Val Gly Asn Gly Arg Tyr Ser Pro Arg Met Arg Pro Gly Ile Lys Ile
            245                 250                 255

Asp Gln Trp Arg Lys Gly Ser Gln Trp Phe Glu Ile Asp Arg Asp Leu
            260                 265                 270

Ala Ile Glu Ile Val Ser Asp Arg Lys Tyr Phe Pro Leu Phe Gln Lys
            275                 280                 285

Tyr Cys Thr Gly Gln Cys Tyr Ser Asp Glu His Tyr Leu Pro Thr Phe
        290                 295                 300

Val Thr Met Lys His Ser Lys Arg Asn Ser Asn Arg Thr Leu Thr Trp
305                 310                 315                 320

Val Asp Trp Ser Arg Gly Gly Pro His Pro Ala Lys Phe Leu Arg Thr
                325                 330                 335

Glu Val Thr Ile Glu Phe Leu Glu Arg Met Arg Ser Gly Ser Lys Cys
            340                 345                 350

Val Tyr Asn Gly Asn His Thr Asn Thr Cys Phe Leu Phe Ala Arg Lys
        355                 360                 365

Phe Trp Pro Asn Ala Leu Asp Arg Leu Leu Arg Phe Ala Pro Lys Ile
    370                 375                 380

Met His Phe Asn Ser
385

<210> SEQ ID NO 17
<211> LENGTH: 411
<212> TYPE: PRT
<213> ORGANISM: Populus Trichocarpa

<400> SEQUENCE: 17

Met Lys Gln Cys Lys Ile Thr Val Phe Leu Lys Asp Leu Ser Ile Arg
1               5                   10                  15

Phe Arg Lys Glu Val Arg Glu Gly Ser Leu Gln Ala Thr Thr Thr Val
            20                  25                  30

Val Leu Cys Leu Ser Met Val Ser Phe Val Val Ile Leu Ala Met Phe
        35                  40                  45

Ile Asn Asn Val Lys Lys Tyr Leu Val Ser Glu Asp Tyr Ser Tyr
    50                  55                  60

Tyr Gln Leu Ala Thr Leu Thr Pro Leu Ser Ser Gly Ser Pro Cys Pro
65                  70                  75                  80

Tyr Phe Leu Cys Asn Ser Phe Leu Ser Pro Ser Leu Gln Pro Leu
                85                  90                  95

Gln Phe Pro Ile Thr Ser Leu Arg Asp Trp Val Thr Pro Lys Glu Leu
            100                 105                 110

Cys His Ser Met Asn Asp Lys Glu Leu Leu Trp Arg Ala Ser Met Val
        115                 120                 125

Pro His Ile Asp Glu Tyr Pro Tyr Asn Arg Thr Pro Lys Val Ala Phe
    130                 135                 140
```

```
Met Phe Leu Thr Arg Gly Ser Leu Pro Leu Ala Pro Leu Trp Glu Met
145                 150                 155                 160

Phe Phe Lys Gly His Glu Gly Leu Tyr Ser Ile Tyr Leu His Lys Ser
            165                 170                 175

Pro Glu Phe Thr Asn Gln His Pro Glu Ser Ser Val Phe Tyr Gln Arg
        180                 185                 190

Gln Ile Pro Ser Lys Pro Ala Glu Trp Gly Arg Ala Thr Met Ile Asp
    195                 200                 205

Ala Glu Arg Arg Leu Leu Asn Ala Leu Leu Asp Phe Ser Asn Glu
210                 215                 220

Arg Phe Val Leu Leu Ser Glu Thr Cys Ile Pro Val Phe Asn Phe Ser
225                 230                 235                 240

Thr Ile Tyr Asn Tyr Leu Met Asn Ser Asn Gln Ser Phe Leu Gly Ser
                245                 250                 255

Phe Asp Asp Pro Arg His Met Gly Arg Gly Arg Tyr Asn Lys Arg Met
            260                 265                 270

Arg Pro Thr Val Thr Leu Ser Asp Trp Arg Lys Gly Ser Gln Trp Phe
        275                 280                 285

Glu Ala His Arg Lys Val Ala Ile Glu Met Ile Ser Asp Val Lys Tyr
    290                 295                 300

Tyr Pro Val Phe Arg Asp His Cys Arg Pro Cys Tyr Met Asp Glu
305                 310                 315                 320

His Tyr Phe Pro Thr Leu Val Thr Lys Ile Ser Pro Glu Leu Asn Ser
                325                 330                 335

Asn Arg Ser Ile Thr Trp Val Asp Trp Ser Gly Gly Gly Ser His Pro
            340                 345                 350

Ala Arg Phe Val Arg Lys Asp Val Ser Glu Ala Phe Leu Asn Gln Ile
        355                 360                 365

Arg Asn Gly Phe Asn Cys Thr Tyr Asn Gly Gly Ile Thr Thr Val Cys
    370                 375                 380

Phe Leu Phe Ala Arg Lys Phe His Pro Ser Thr Leu Asp Pro Leu Leu
385                 390                 395                 400

Arg Ile Ala Pro Gly Leu Leu Gly Phe Arg Ser
                405                 410

<210> SEQ ID NO 18
<211> LENGTH: 343
<212> TYPE: PRT
<213> ORGANISM: Populus Trichocarpa

<400> SEQUENCE: 18

Met Leu Ser Ser Pro Ile Leu Tyr Ser Phe Ser Leu Leu Leu Ser Phe
1               5                   10                  15

Ser Leu Ile Tyr Leu Phe Thr Pro Gln Ile Leu Val Pro Leu Gln Asn
            20                  25                  30

Ala Leu Ser Tyr Glu Leu Asp Asp Pro Thr Leu Phe Lys Lys Ala Leu
        35                  40                  45

Lys Pro Cys Lys Thr Ile Pro Pro Leu Ala Thr Asn Asn Pro Thr Pro
50                  55                  60

Lys Ile Ala Phe Leu Phe Leu Thr Asn Ser Asp Leu Ser Phe Ala Pro
65                  70                  75                  80

Leu Trp Glu Arg Phe Phe Glu Gly Tyr Asn Asn Leu Tyr Asn Ile Tyr
                85                  90                  95

Val His Ala Asp Pro Phe Ser Lys Val Ser Asn Pro Asp Gly Ile Phe
            100                 105                 110
```

```
Lys Asn Arg Phe Ile Pro Gly Lys Thr Glu Arg Gly Ser Pro Ser
            115                 120                 125

Leu Ile Leu Ala Glu Lys Arg Leu Leu Ala Arg Ala Ile Leu Asp Asp
130                 135                 140

Pro Leu Asn Leu Tyr Phe Ala Leu Val Ser Gln His Cys Val Pro Leu
145                 150                 155                 160

His Ser Phe Gln Tyr Ile His Asp Thr Leu Phe Gly His Asn Ile Leu
                165                 170                 175

Lys Thr Phe Thr Thr Gln Ser Arg His Gln Ser Phe Ile Glu Ile Leu
            180                 185                 190

Ser Glu Asp Pro Asn Leu Pro Asp Arg Tyr Asn Ala Arg Gly Glu Asn
            195                 200                 205

Ile Met Leu Pro Glu Ile Pro Tyr Glu Lys Phe Arg Val Gly Ser Gln
210                 215                 220

Phe Phe Val Leu Ala Lys Arg His Ala Leu Leu Val Leu Lys Asp Arg
225                 230                 235                 240

Lys Leu Trp Arg Lys Phe Lys Leu Pro Cys Leu Asn Thr Glu Ser Cys
                245                 250                 255

Tyr Pro Glu Glu His Tyr Phe Pro Thr Leu Leu Ser Met Lys Asn Pro
            260                 265                 270

Arg Gly Cys Ser His Tyr Thr Leu Thr Asn Val Asn Trp Thr Asp Cys
            275                 280                 285

Phe Asp Gly His Pro His Leu Tyr Gln Ala Glu Glu Val Ser Pro Asn
290                 295                 300

Leu Val His Gly Leu Arg Gln Ser Asn Ser Ser Tyr Ser Tyr Phe Phe
305                 310                 315                 320

Ala Arg Lys Phe Ala Pro Asp Cys Leu Gln Pro Leu Met Glu Met Ala
                325                 330                 335

Asp Asp Val Ile Phe Lys Asp
            340

<210> SEQ ID NO 19
<211> LENGTH: 386
<212> TYPE: PRT
<213> ORGANISM: Populus Trichocarpa

<400> SEQUENCE: 19

Met Thr Lys Lys Ser Ser Leu Leu Pro Ile Leu Leu Gln Gln Ser Arg
1               5                   10                  15

Arg Arg Val Ile Trp Ser Gly Trp Lys Leu Val Ile Ile Leu Ser Met
            20                  25                  30

Gly Leu Cys Val Phe Ala Leu Phe Arg Ile His Leu Ser Ser Pro Pro
            35                  40                  45

Glu Thr Leu Leu Ser Arg Arg Arg Ser Phe Ser Arg Glu Val Val Phe
    50                  55                  60

Ser Gly Pro Pro Lys Val Ala Phe Leu Phe Leu Val Arg Arg Gly Leu
65                  70                  75                  80

Pro Leu Asp Phe Leu Trp Gly Ser Phe Phe Glu Asn Ala Asp Thr Gly
                85                  90                  95

Asn Phe Ser Ile His Val His Ser Glu Pro Gly Phe Glu Phe Asp Glu
            100                 105                 110

Ser Thr Thr Arg Ser His Phe Phe Tyr Gly Arg Gln Leu Lys Asn Ser
            115                 120                 125

Ile Gln Val Ile Trp Gly Glu Ser Ser Met Ile Glu Ala Glu Arg Leu
```

```
            130                 135                 140
Leu Leu Asp Ala Ala Leu Glu Asp Pro Ala Asn Gln Arg Phe Val Leu
145                 150                 155                 160

Leu Ser Asp Ser Cys Val Pro Leu Tyr Asn Phe Ser Tyr Ile Tyr Ser
                165                 170                 175

Tyr Leu Met Ala Ser Pro Arg Ser Phe Val Asp Ser Phe Leu Asp Val
            180                 185                 190

Lys Glu Gly Arg Tyr His Pro Lys Met Ser Pro Val Ile Pro Lys Asp
        195                 200                 205

Lys Trp Arg Lys Gly Ser Gln Trp Ile Ala Leu Ile Arg Ser His Ala
    210                 215                 220

Glu Val Ile Val Asp Val Val Ile Leu Pro Val Phe Lys Lys Leu
225                 230                 235                 240

Cys Lys Arg Arg Pro Pro Leu Asp Ala Ser Lys Gly Lys Leu Asn Ile
                245                 250                 255

Lys Leu Gln Lys Gln His Asn Cys Ile Pro Asp Glu His Tyr Val Gln
            260                 265                 270

Thr Leu Leu Ser Met Ser Glu Leu Glu Gly Glu Leu Glu Arg Arg Thr
        275                 280                 285

Val Thr Tyr Thr Val Trp Asn Gln Ser Ala Thr Lys Met Glu Asn Lys
    290                 295                 300

Gly Trp His Pro Lys Thr Phe Ser Tyr Ala Asn Ala Ser Pro Arg Lys
305                 310                 315                 320

Ile Lys Glu Ile Lys Gly Ile Asn His Ile Asp Tyr Glu Thr Glu Tyr
                325                 330                 335

Arg Thr Glu Trp Cys Arg Thr Asn Ser Thr Phe Val Pro Cys Phe Leu
            340                 345                 350

Phe Ala Arg Lys Phe Ser Arg Gly Ala Ala Met Arg Leu Leu Ser Asp
        355                 360                 365

Gly Val Ala Gly Gln Phe Asp Ala Ser Ser Ile Leu Ala Arg Ser Ala
    370                 375                 380

Pro Asp
385

<210> SEQ ID NO 20
<211> LENGTH: 396
<212> TYPE: PRT
<213> ORGANISM: Populus Trichocarpa

<400> SEQUENCE: 20

Met Lys Asp Thr Asp Asp Gln Gln Leu Arg Pro Gln Thr Ser Trp Lys
1               5                   10                  15

Leu Gln Val His Leu Gln Asn Phe Ile Phe Tyr Leu Leu Val Phe Gly
                20                  25                  30

Cys Gly Leu Ala Phe Gly Ile Ala Arg Thr Ser Tyr Ile Arg Asp Ile
            35                  40                  45

Ser Phe Asn Phe Gln Leu Asp Gln Phe Ser Asn Asn Arg Thr Asn Thr
        50                  55                  60

Ser Leu Ser Asn Ser Ser Ser Pro Pro Phe Ile Thr Ile Asp Arg
65                  70                  75                  80

Asn Arg Thr Gly Arg Ile Gly Leu Glu Glu Phe Leu Arg Ala Pro Asn
                85                  90                  95

Val Ser His Asp Met Asn Glu Glu Glu Leu Leu Trp Arg Ala Ser Met
            100                 105                 110
```

```
Val Pro Arg Leu Pro Asn Tyr Pro Phe Gln Leu Val Pro Lys Val Ala
            115                 120                 125

Phe Leu Phe Leu Thr Lys Gly Pro Leu Pro Leu Ala Pro Leu Trp Asp
        130                 135                 140

Leu Phe Phe Lys Gly His Gln Gly Leu Tyr Ser Ile Phe Val His Ser
145                 150                 155                 160

Asn Pro Ser Phe Asn Gly Asn Tyr Thr Glu Glu Asp Ser Val Phe
                165                 170                 175

Arg Gly Arg Lys Ile Pro Ser Lys Glu Val Gln Trp Gly Lys Phe Ser
                180                 185                 190

Met Val Glu Ala Glu Arg Arg Leu Leu Ala Asn Ala Leu Leu Asp Phe
            195                 200                 205

Ser Asn Gln Arg Phe Val Leu Leu Ser Glu Ser Cys Ile Pro Leu Phe
        210                 215                 220

Asn Phe Ser Thr Ile Tyr Ser Tyr Leu Met Gly Ser Thr Thr Thr Phe
225                 230                 235                 240

Ile Glu Val Tyr Asp Leu Pro Gly Pro Val Gly Arg Gly Arg Tyr Asn
                245                 250                 255

His Arg Met Arg Pro Val Ile Gln Leu Asp Lys Trp Arg Lys Gly Ser
            260                 265                 270

Gln Trp Val Glu Met Asp Arg Gln Leu Ala Val Glu Val Val Ser Asp
        275                 280                 285

Arg Lys Tyr Phe Pro Thr Phe Arg Lys Phe Cys Lys Val Ser Cys Tyr
        290                 295                 300

Ser Asp Glu His Tyr Leu Pro Thr Phe Val Asn Met Lys Ser Arg Lys
305                 310                 315                 320

Lys Asn Ser Asn Arg Ser Leu Thr Trp Val Asp Trp Ser Arg Gly Gly
                325                 330                 335

Pro His Pro Arg Lys Phe Gly Arg Leu Asp Ile Thr Val Asp Phe Leu
            340                 345                 350

Glu Arg Leu Arg Lys Trp Arg Arg Cys Glu Asn Asn Gly Arg Trp Thr
        355                 360                 365

Asn Ile Cys Tyr Leu Phe Ala Arg Lys Phe Thr Pro Ala Ala Leu Asp
370                 375                 380

Arg Leu Met Arg Phe Ala Pro Lys Val Met Gln Phe
385                 390                 395

<210> SEQ ID NO 21
<211> LENGTH: 352
<212> TYPE: PRT
<213> ORGANISM: Populus Trichocarpa

<400> SEQUENCE: 21

Met Phe Ser Leu Thr Leu Pro Pro Pro Gln Leu Pro Pro Pro
1               5                   10                  15

Gln Val Leu Leu Leu Gln Pro Pro Pro Arg Pro Pro Pro
            20                  25                  30

Pro Leu Ile Lys Pro Phe Pro Pro Ala Ser Leu Pro Thr Leu Leu
        35                  40                  45

Pro Asp Val Arg Pro Pro Leu Val His Lys Met Asp Asp Glu Leu
        50                  55                  60

Phe Ser Arg Ala Ser Met Ile Arg Gly Ser Gln Asn Phe Gly Arg Asp
65                  70                  75                  80

Gln His Val Arg Lys Val Ala Phe Met Phe Leu Thr Lys Gly Pro Ile
                85                  90                  95
```

Pro Leu Ala Pro Leu Trp Glu Lys Phe Phe Arg Gly His Glu Gly Leu
                100                 105                 110

Tyr Thr Ile Tyr Val His His Pro Ser Tyr Asn Asp Ser Val Pro
            115                 120                 125

Glu Gly Ser Val Phe His Gly Arg Arg Ile Pro Ser Lys Pro Val Glu
130                 135                 140

Trp Gly Arg Pro Ser Met Ile Asp Ala Glu Arg Arg Leu Leu Ala Asn
145                 150                 155                 160

Ala Leu Leu Asp Val Ser Asn Glu Arg Phe Val Leu Leu Ser Glu Thr
                165                 170                 175

Cys Ile Pro Ile Phe Asn Phe Thr Thr Val Tyr Asn Tyr Leu Val Asn
            180                 185                 190

Ala Lys Glu Ser Phe Ile Gly Ser Tyr Asp Asp Pro Arg Lys Val Gly
                195                 200                 205

Arg Gly Arg Tyr Asn Pro Lys Met Leu Pro Ala Ile Thr Ile Ser Asp
210                 215                 220

Trp Arg Lys Gly Ser Gln Trp Phe Glu Val His Arg Lys Leu Ala Val
225                 230                 235                 240

Glu Ile Ile Ser Asp Thr Lys Tyr Tyr Arg Ile Phe Ser Glu Tyr Cys
                245                 250                 255

Ser Pro Pro Cys Tyr Met Asp Glu His Tyr Ile Pro Thr Leu Val Asn
            260                 265                 270

Ile Arg Cys Pro Glu Gln Asn Ser Asn Arg Ser Ile Thr Trp Val Asp
            275                 280                 285

Trp Ser Lys Ala Gly Pro His Pro Gly Arg Phe Val Lys Gln Asp Ile
            290                 295                 300

Ser Asp Glu Phe Leu Asp Arg Ile Arg Phe Gly Glu Asn Cys Thr Tyr
305                 310                 315                 320

Asn Gly Asn Ala Ser Ser Leu Cys Phe Leu Phe Ala Arg Lys Phe Leu
                325                 330                 335

Pro Gly Thr Leu Gln Pro Phe Leu His Leu Ala Pro Thr Leu Leu His
            340                 345                 350

<210> SEQ ID NO 22
<211> LENGTH: 385
<212> TYPE: PRT
<213> ORGANISM: Populus Trichocarpa

<400> SEQUENCE: 22

Met Gln Ser Arg Val Val Pro Leu Glu Glu Gly Lys Asp Pro Ala Val
1               5                   10                  15

Ser Ile Lys Ala Ser Gln Ser Lys His Ser Pro Ile Arg Leu Leu Gln
                20                  25                  30

Phe Phe Leu Leu Phe Leu Ala Val Cys Ile Ser Phe Ser Ile Ile Ser
            35                  40                  45

Met Tyr Thr Ile Lys Arg Ser Gly Val Gln Thr Ala Gly Thr Thr Val
50                  55                  60

Lys Pro Ala Phe Lys His Cys Phe Asp Glu Pro Asn Thr Leu Asp Arg
65                  70                  75                  80

Trp Ile Arg Arg Pro Leu Asn Leu Leu His Lys Met Ser Asp Glu Glu
                85                  90                  95

Leu Phe Trp Arg Ala Ser Phe Val Pro Arg Ile Lys Lys Tyr Pro Phe
            100                 105                 110

Lys Arg Val Pro Lys Ile Ala Phe Met Phe Leu Thr Lys Gly Pro Leu

|   |   | 115 |   |   |   | 120 |   |   |   | 125 |   |
|---|---|---|---|---|---|---|---|---|---|---|---|

Pro Leu Ala Pro Leu Trp Glu Lys Phe Leu Lys Gly His Glu Gly Leu
130                 135                 140

Tyr Ser Val Tyr Ile His Ser Leu Pro Thr Phe Glu Ala Lys Phe Pro
145                 150                 155                 160

Pro Ser Ser Val Phe His Arg Arg Gln Ile Pro Ser Gln Ile Ser Glu
                165                 170                 175

Trp Gly Lys Met Ser Met Cys Asp Ala Glu Arg Arg Leu Leu Ala Asn
            180                 185                 190

Ala Leu Leu Asp Ile Leu Asn Glu Arg Phe Val Leu Val Ser Glu Ser
        195                 200                 205

Cys Ile Pro Leu Phe Asn Phe Thr Phe Val Tyr Gly Tyr Ile Met Arg
    210                 215                 220

Ser Lys His Ser Phe Ile Gly Ala Phe Asp Asp His Gly Pro Tyr Gly
225                 230                 235                 240

Arg Gly Arg Tyr Asn Glu Asn Met Ala Pro Glu Val Asn Ile Thr Asn
                245                 250                 255

Trp Arg Lys Gly Ser Gln Trp Phe Glu Ile Asn Arg Lys Leu Ala Val
            260                 265                 270

Asn Ile Val Glu Asp Thr Thr Phe Tyr Pro Lys Phe Glu Glu Phe Cys
        275                 280                 285

Lys Pro His Cys Tyr Val Asp Glu His Tyr Phe Pro Thr Met Leu Thr
    290                 295                 300

Val Arg Thr Ala Pro Leu Leu Ala Asn Arg Thr Leu Thr Trp Val Asp
305                 310                 315                 320

Trp Ser Arg Gly Gly Ala His Pro Ala Thr Phe Gly Arg Ala Asp Ile
                325                 330                 335

Lys Glu Glu Phe Phe Lys Lys Val His Glu Asp Lys His Cys Ile Tyr
            340                 345                 350

Asn Asn Gln Ser Thr Ser Ile Cys Phe Leu Phe Ala Arg Lys Phe Ala
        355                 360                 365

Pro Ser Ala Leu Glu Pro Leu Leu His Ile Ser Arg Asn Val Leu Gly
    370                 375                 380

Phe
385

<210> SEQ ID NO 23
<211> LENGTH: 424
<212> TYPE: PRT
<213> ORGANISM: Populus Trichocarpa

<400> SEQUENCE: 23

Met Lys Thr Ser Gln Val Trp Arg Leu Gly Met Gly Asp Met Gln Ile
1               5                   10                  15

Leu Pro Val Ala Arg His Arg Pro Pro Ser Lys Arg Pro Thr Trp Ile
            20                  25                  30

Ile Val Leu Val Ser Met Val Ser Leu Phe Leu Val Cys Ala Tyr Ile
        35                  40                  45

Tyr Pro Pro Gln Ser Arg Asn Ala Cys Tyr Val Phe Ser Ser Arg Gly
    50                  55                  60

Cys Gln Val Leu Thr Asp Trp Leu Pro Pro Ala Pro Thr Arg Glu Leu
65                  70                  75                  80

Thr Asp Glu Glu Ile Ala Ser Arg Val Val Ile Arg Glu Ile Leu Ser
                85                  90                  95

```
Ala Ser Leu Thr Pro Thr Lys Asn Ala Lys Ile Ala Phe Met Phe Leu
            100                 105                 110

Thr Pro Gly Pro Leu Pro Phe Glu Lys Leu Trp Asp Lys Phe Phe Ser
        115                 120                 125

Gly His Glu Asp Arg Phe Ser Val Tyr Val His Ala Ser Lys Glu Lys
    130                 135                 140

Pro Val His Val Ser Arg Tyr Phe Val Asn Gln Asp Ile Arg Ser Asp
145                 150                 155                 160

Gln Val Ile Trp Gly Lys Ile Ser Met Ile Asp Ala Glu Arg Arg Leu
                165                 170                 175

Leu Ala Asn Ala Leu Arg Asp Pro Asp Asn Gln His Phe Val Leu Leu
            180                 185                 190

Ser Asp Ser Cys Val Pro Leu Tyr Lys Phe Asp Tyr Ile Tyr Asn Tyr
        195                 200                 205

Leu Met Phe Thr Asn Ile Ser Tyr Val Asp Arg Phe Tyr Asp Pro Gly
210                 215                 220

Pro His Gly Asn Gly Arg Tyr Ser Glu His Met Leu Pro Glu Val Glu
225                 230                 235                 240

Met Lys Asp Phe Ser Lys Gly Ala Gln Trp Phe Ser Met Lys Arg Gln
                245                 250                 255

His Ala Val Met Val Leu Ala Asp Ser Leu Tyr Tyr Ser Lys Phe Arg
            260                 265                 270

Asp Tyr Cys Lys Pro Gly Leu Glu Gly Lys Asn Cys Ile Ala Asp Glu
        275                 280                 285

His Tyr Leu Pro Thr Tyr Phe His Met Val Asp Pro Gly Gly Ile Ala
    290                 295                 300

Asn Trp Ser Val Thr His Val Asp Trp Ser Glu Arg Lys Trp His Pro
305                 310                 315                 320

Lys Leu Tyr Arg Ser Gln Asp Val Thr Tyr Asp Leu Leu Arg Asn Ile
                325                 330                 335

Thr Ser Ile Asp Leu Ser Ile His Val Thr Ser Asp Glu Lys Val Gln
            340                 345                 350

Phe Phe Gln Gly Tyr Leu Gly Thr Glu Phe Phe His Lys Leu Leu Ala
        355                 360                 365

Asp Val Phe Val Ser Pro Phe Pro Cys Ala Phe Cys Arg Arg Lys Cys
    370                 375                 380

Arg Cys Ser Leu Ala Tyr Gly Met Val Ser His Asp His Val Thr Cys
385                 390                 395                 400

Leu Arg Gly Asn Ser Thr Lys Lys Leu Leu Met Ile Cys Cys Ser Phe
                405                 410                 415

Ser Arg Thr Thr Gln His Phe Glu
            420

<210> SEQ ID NO 24
<211> LENGTH: 386
<212> TYPE: PRT
<213> ORGANISM: Populus Trichocarpa

<400> SEQUENCE: 24

Met Thr Lys Lys Ser Ser Leu Leu Pro Ile Leu Leu Gln Gln Ser Arg
1               5                   10                  15

Arg Arg Val Ile Trp Ser Gly Trp Lys Leu Val Ile Ile Leu Ser Met
            20                  25                  30

Gly Leu Cys Val Phe Ala Leu Phe Arg Ile His Leu Ser Ser Pro Pro
        35                  40                  45
```

```
Glu Thr Leu Leu Ser Arg Arg Arg Ser Phe Ser Arg Glu Val Val Phe
        50                  55                  60

Ser Gly Pro Pro Lys Ile Ala Phe Leu Phe Leu Val Arg Arg Gly Leu
65                  70                  75                  80

Pro Leu Asp Phe Leu Trp Gly Ser Phe Leu Glu Asn Ala Asp Thr Gly
                85                  90                  95

Asn Phe Ser Ile Tyr Val His Ser Glu Pro Gly Phe Glu Phe Asp Glu
            100                 105                 110

Ser Thr Thr Arg Ser Arg Phe Phe Tyr Gly Arg Gln Leu Lys Asn Ser
                115                 120                 125

Ile Gln Val Ile Trp Gly Glu Ser Ser Met Ile Glu Ala Glu Arg Leu
130                 135                 140

Leu Leu Asp Ala Ala Leu Glu Asp Pro Ala Asn Gln Arg Phe Val Leu
145                 150                 155                 160

Leu Ser Asp Ser Cys Val Pro Leu Tyr Asn Phe Ser Tyr Ile Tyr Ser
                165                 170                 175

Tyr Leu Met Ala Ser Pro Arg Ser Phe Val Asp Ser Phe Leu Asp Val
                180                 185                 190

Lys Glu Gly Arg Tyr His Pro Lys Met Ser Pro Val Ile Pro Lys Asp
                195                 200                 205

Lys Trp Arg Lys Gly Ser Gln Trp Ile Ala Leu Ile Arg Ser His Ala
210                 215                 220

Glu Val Ile Val Asp Asp Val Val Ile Leu Pro Val Phe Lys Lys Leu
225                 230                 235                 240

Cys Lys Arg Arg Pro Pro Leu Asp Ala Thr Lys Gly Lys Leu Asn Ile
                245                 250                 255

Lys Leu Gln Lys Gln His Asn Cys Ile Pro Asp Glu His Tyr Val Gln
                260                 265                 270

Thr Leu Leu Ser Met Ser Gly Leu Glu Gly Glu Leu Glu Arg Arg Thr
                275                 280                 285

Val Thr Tyr Thr Val Trp Asn Gln Ser Ala Thr Lys Met Glu Asn Lys
        290                 295                 300

Gly Trp His Pro Lys Thr Phe Ser Tyr Ala Asn Ala Ser Pro Gln Lys
305                 310                 315                 320

Ile Met Glu Ile Lys Gly Ile Asn His Ile Asp Tyr Glu Thr Glu Tyr
                325                 330                 335

Arg Thr Glu Trp Cys Arg Thr Asn Ser Thr Phe Val Pro Cys Phe Leu
                340                 345                 350

Phe Ala Arg Lys Phe Ser Arg Gly Ala Ala Met Arg Leu Leu Ser Asp
                355                 360                 365

Gly Val Thr Gly Pro Phe Asp Ala Ser Ser Ile Leu Ala Arg Ser Ala
        370                 375                 380

Pro Asp
385

<210> SEQ ID NO 25
<211> LENGTH: 283
<212> TYPE: PRT
<213> ORGANISM: Populus Trichocarpa

<400> SEQUENCE: 25

Met Leu Ser Pro Thr Pro Leu Ser Leu Leu Cys Thr Ile Phe Leu Thr
1               5                   10                  15

Lys Asn Leu Pro Lys Leu Lys Ile Lys Thr Pro Ile Ser Pro Gln Pro
```

```
            20                  25                  30
Pro Pro His Pro Pro Ser Leu Pro Pro Pro Gln Asp Asp Asp Ser
        35                  40                  45

Leu Leu His Leu Ala Ser Gln Val Asn Pro Arg Pro Lys Ser Pro Lys
 50                  55                  60

Lys Leu Ala Phe Leu Phe Leu Thr Thr Thr Pro Leu Pro Phe Ala Pro
 65                  70                  75                  80

Pro Trp Glu Leu Tyr Phe Asn Gln Ser Arg Thr Val Phe Thr Asp Lys
                 85                  90                  95

Val Ile His Ser Lys Leu Ala Lys Arg Ser Thr Pro Thr Leu Ile Ser
                100                 105                 110

Ala Val Arg Arg Leu Leu Ser His Ala Leu Leu His Asp Pro Ser Thr
            115                 120                 125

Ser Met Phe Ala Leu Leu Ser Pro Ser Tyr Gly Arg Arg Val Glu Ser
        130                 135                 140

Met Leu Pro Glu Val Gly Phe Lys Asp Phe Arg Ile Gly Ser Gln Phe
145                 150                 155                 160

Arg Val Leu Thr Arg Lys His Ala Arg Met Val Val Arg Asp Met Arg
                165                 170                 175

Ile Trp Pro Lys Phe Asn Gln Thr Cys Leu Arg Glu Asp Thr Cys Tyr
            180                 185                 190

Pro Glu Glu Asn Tyr Phe Pro Thr Leu Ile His Met Gln Asp Pro Arg
        195                 200                 205

Gly Val Ser Ala Gly Gly His Pro Arg Lys Tyr Lys Ala Ser Glu Val
    210                 215                 220

Gly Pro Asp Leu Ile Met Ser Leu Arg Asn Arg Arg Pro Arg Tyr Gly
225                 230                 235                 240

Tyr Glu Gly Ile Asn Gly Ser Asp Leu Ser Val Met Lys Arg Asn Asp
                245                 250                 255

Pro Phe Leu Phe Ala Arg Lys Phe Ser Pro Asp Ser Ile Gln Pro Leu
            260                 265                 270

Ile Ser Ile Ala Lys Asp Ile Ile Leu Asn Asp
        275                 280

<210> SEQ ID NO 26
<211> LENGTH: 392
<212> TYPE: PRT
<213> ORGANISM: Oryza sativa

<400> SEQUENCE: 26

Met Pro Ala Ala Lys Arg Ser Ala Ser Ala Gly Ser Val Leu Ala Leu
 1               5                  10                  15

Thr Val Ala Gly Arg Arg Ala Ala Arg Ala Arg Leu Cys Leu Arg Leu
                 20                  25                  30

Ala Ala Pro Leu Ser Phe Leu Leu Leu Ala Ala Leu Leu Arg Thr
            35                  40                  45

Gln Pro Leu Pro Ala Pro Pro Ser Ala Pro Pro Ser Gly Gly Pro
         50                  55                  60

Ala Arg Val Ala Phe Leu Phe Leu Val Arg Ala Gly Val Pro Leu Asp
 65                  70                  75                  80

Phe Leu Trp Asp Ala Phe Phe Arg Asn Gly Glu Gly Lys Phe Ser
                 85                  90                  95

Val Tyr Val His Ser Ala Pro Gly Phe Gln Leu Asp Arg Thr Thr Thr
                100                 105                 110
```

```
Gly Ser Ser Tyr Phe Tyr Gly Arg Gln Leu Ala Arg Ser Val Lys Val
            115                 120                 125
Ala Trp Gly Glu Pro Thr Met Val Glu Ala Glu Arg Met Leu Phe Ala
130                 135                 140
Ala Ala Leu Glu Asp Pro Ala Asn Gln Arg Phe Val Leu Leu Ser Asp
145                 150                 155                 160
Ser Cys Val Pro Leu Tyr Asn Phe Ser Tyr Ile Tyr Thr Tyr Leu Met
                165                 170                 175
Ala Ser Thr Lys Ser Phe Val Asp Ser Phe Val Asp Lys Thr Glu Lys
            180                 185                 190
Arg Tyr Asn Pro Ser Met Ser Pro Val Ile Leu Lys Asp Lys Trp Arg
        195                 200                 205
Lys Gly Ser Gln Trp Val Ala Leu Thr Arg Arg His Ala Glu Val Val
    210                 215                 220
Val Gly Asp Lys Leu Val Leu Gln Val Phe Arg Arg His Cys Lys Met
225                 230                 235                 240
Val Val Thr Lys Ala Leu Leu Gly Gln Lys Pro Asn Tyr Arg Arg Leu
                245                 250                 255
Gly Phe Gly Leu Arg Arg Lys Gln Ile Ser Lys Gly Ser Thr Arg Met
            260                 265                 270
Glu His Asp Cys Ile Pro Asp Glu His Tyr Val Gln Thr Leu Phe Ser
        275                 280                 285
Ile Asn Gly His Glu Asn Glu Leu Glu Arg Arg Thr Leu Thr Tyr Thr
    290                 295                 300
Ser Trp Asn Gln Ser Ser Asp Pro Lys Asp Lys Met Thr Trp His Pro
305                 310                 315                 320
Met Thr Phe Glu Tyr Glu Ser Ala Ser Pro Glu Gln Ile Asn Ser Ile
                325                 330                 335
Lys Gly Ile Asp His Val Asn Tyr Gln Met Glu His Arg Thr Glu Trp
            340                 345                 350
Cys Gln Cys Asn Thr Thr Ser Val Pro Cys Phe Leu Phe Ala Arg Lys
        355                 360                 365
Phe Ser Tyr Ser Ala Ala Met His Leu Leu Glu Ala Gly Thr Val Gly
    370                 375                 380
Pro Leu Lys Ser Ala Leu Leu Ala
385                 390

<210> SEQ ID NO 27
<211> LENGTH: 391
<212> TYPE: PRT
<213> ORGANISM: Zea mays

<400> SEQUENCE: 27

Met Pro Val Lys Arg Ser Ala Ser Ala Leu Ala Leu Pro Pro Val Gly
1               5                   10                  15
Arg Arg Ala Arg Ala Arg Leu Cys Ile Arg Leu Ala Ala Pro Leu Ser
            20                  25                  30
Phe Leu Leu Leu Phe Val Ala Leu Phe His Ala Gln Pro Leu Leu Gly
        35                  40                  45
Val Pro Pro Ala Ala Gln Pro Pro Ser Ala Gly Pro Gly Lys Val Ala
    50                  55                  60
Phe Leu Phe Leu Val Arg Ala Gly Val Pro Leu Asp Phe Leu Trp Asp
65                  70                  75                  80
Ala Phe Phe Arg Asn Gly Glu Glu Gly Lys Phe Ser Val Tyr Val His
                85                  90                  95
```

```
Ser Ala Pro Gly Phe Gln Leu Asp Arg Thr Thr Gly Ser Pro Tyr
            100                 105                 110

Phe Tyr Gly Arg Gln Leu Ala Arg Ser Val Lys Val Trp Gly Glu
            115                 120                 125

Ala Thr Met Val Glu Ala Glu Arg Met Leu Phe Ala Ala Leu Gln
130                 135                 140

Asp Pro Ala Asn Gln Arg Phe Val Leu Leu Ser Asp Ser Cys Val Pro
145                 150                 155                 160

Leu Tyr Asn Phe Ser Ser Ile Tyr Thr Tyr Leu Met Ala Ser Pro Lys
                165                 170                 175

Ser Phe Val Asp Ser Phe Val Asp Lys Thr Glu Lys Arg Tyr Asn Gln
            180                 185                 190

Asn Met Ser Pro Ala Ile Pro Lys Asp Lys Trp Arg Lys Gly Ser Gln
            195                 200                 205

Trp Val Val Leu Ile Arg Lys His Ala Glu Val Val Gly Asp Lys
            210                 215                 220

Asn Val Leu Lys Val Phe Arg Arg His Cys Lys Met Val Val Thr Lys
225                 230                 235                 240

Ser Leu Phe Arg Arg Pro Asn Ala Arg Gln Leu Gly Phe Thr Phe
                245                 250                 255

Arg Arg Lys Gln Ile Leu Lys Gly Val Ala Gln Gln Glu His Asp Cys
            260                 265                 270

Ile Pro Asp Glu His Tyr Val Gln Thr Leu Phe Ser Ile Lys Gly Leu
            275                 280                 285

Glu Asp Glu Leu Glu Arg Arg Thr Leu Thr Tyr Thr Ser Trp Asn Gln
290                 295                 300

Ser Ser Asn Pro Lys Asp Lys Met Thr Trp His Pro Met Lys Phe Glu
305                 310                 315                 320

Tyr Asp Thr Ser Ser Pro Glu His Ile Asn Ala Ile Lys Arg Ile Asp
                325                 330                 335

His Val Asn Tyr Gln Met Glu His Arg Thr Glu Trp Cys Gln Cys Asn
            340                 345                 350

Gly Thr Ser Ala Pro Cys Phe Leu Phe Ala Arg Lys Phe Ser Tyr Ser
            355                 360                 365

Ala Ala Met His Leu Leu Glu Gln Gly Ala Ile Gly Thr Pro Lys Ser
            370                 375                 380

Ala Gln Leu Met Ile Asn Phe
385                 390

<210> SEQ ID NO 28
<211> LENGTH: 365
<212> TYPE: PRT
<213> ORGANISM: Populus Trichocarpa

<400> SEQUENCE: 28

Met Lys Ser Ser Lys Pro Arg His Leu Leu Trp Phe Gly Phe Lys Met
1               5                   10                  15

Val Ile Ala Leu Cys Phe Leu Ser Tyr Gly Leu Phe Ala Tyr Leu Lys
            20                  25                  30

Leu His Ser His Val Lys Leu Pro Ser Leu His Pro Pro Ala Phe His
            35                  40                  45

Thr Ser Pro Ser Arg Tyr His His Phe Glu Gly Thr Pro Lys Ile
50                  55                  60

Ala Phe Leu Phe Leu Ala Arg Arg Asp Leu Pro Leu Asp Phe Leu Trp
```

```
                65                  70                  75                  80
Asp Ser Phe Phe Lys Asn Val Asp Ala Ala Lys Phe Ser Ile Tyr Ile
                    85                  90                  95

His Ser Thr Pro Gly Phe Val Phe Asn Glu Thr Thr Arg Ser Ala
            100                 105                 110

Phe Phe Tyr Gly Gln Gln Leu Asn Tyr Ser Ile Gln Val Ile Trp Gly
                115                 120                 125

Glu Ser Ser Met Ile Glu Ala Glu Lys Leu Leu Leu Ala Ala Leu
130                 135                 140

His Asp Pro Ala Asn Gln Arg Phe Val Leu Leu Ser Asp Ser Cys Val
145                 150                 155                 160

Pro Leu Tyr Asn Phe Ser Tyr Leu Tyr Ser Tyr Leu Met Ser Ser
                165                 170                 175

Lys Ser Phe Val Asp Ser Phe Ile Asp Val Glu Glu Asp Arg Tyr Ser
                180                 185                 190

Pro Lys Met Ser Pro Val Ile Arg Arg Asp Lys Trp Arg Lys Gly Ser
                195                 200                 205

Gln Trp Ile Thr Leu Val Arg Arg His Ala Lys Met Val Ala Glu Asp
    210                 215                 220

Tyr Phe Val Phe Pro Ile Phe Lys Glu Phe Cys Lys Arg Trp Pro Pro
225                 230                 235                 240

Lys Gly Val Asp Asp Arg Lys Glu Ile His Gln Ile Leu Met Asn Gly
                245                 250                 255

Leu Gly Asp Glu Leu Glu Arg Arg Thr Leu Thr Phe Thr Met Trp Asn
                260                 265                 270

His Ser Val Thr Lys Ala Gln Thr Ser Trp His Pro Val Thr Phe Asp
            275                 280                 285

Tyr Asp Asp Ala Ser Ala Lys Lys Ile Lys Glu Ile Lys Val Ile Asn
                290                 295                 300

Ser Ile Ser Arg Lys Gln Gly Asn Gln Ser Glu Met Cys His Val Asn
305                 310                 315                 320

Asn Arg His Thr Pro Cys Phe Leu Phe Ala Arg Lys Phe Thr Tyr Arg
                325                 330                 335

Ala Ala Leu His Leu Leu Thr Gln Asp Leu Val Gly Ser Leu Ile Leu
                340                 345                 350

Leu His His Lys Thr Tyr His His Glu Gln Leu His Tyr
                355                 360                 365

<210> SEQ ID NO 29
<211> LENGTH: 388
<212> TYPE: PRT
<213> ORGANISM: Eucalyptus grandis

<400> SEQUENCE: 29

Met Gly Lys Lys Arg Ala Ser Leu Pro Ile Arg Gln Leu Leu Val Leu
1               5                   10                  15

Arg Ser Lys Leu Val Phe Ser Met Phe Leu Leu Phe Cys Val Phe Ala
                20                  25                  30

Phe Ala Arg Leu Asn Trp Pro Lys Ser Gly Ser Ser Thr Asn Glu Ser
            35                  40                  45

Ser Asn Glu Glu Lys Ser Lys Leu Glu Thr Asn Pro Lys Ile Ala Phe
        50                  55                  60

Leu Phe Leu Ala Arg Lys Asn Ile Pro Leu Asp Phe Met Trp Gly Ala
65                  70                  75                  80
```

```
Phe Phe Gln Glu Ala Asn Val Lys Asn Phe Ser Ile Tyr Ile His Ser
                85                  90                  95

Glu Pro Gly Phe Val Phe Asn Glu Ser Thr Ser Met Ser Pro Phe Phe
            100                 105                 110

Tyr Gly Cys Gln Leu Asn Asp Ser Val Lys Val Ala Trp Gly Gly Ser
            115                 120                 125

Ser Met Ile Glu Ala Glu Arg Leu Leu Leu Lys Val Ala Leu Arg Asp
        130                 135                 140

Pro Ala Asn Gln Arg Phe Val Leu Leu Ser Asp Ser Cys Leu Pro Leu
145                 150                 155                 160

Tyr Glu Phe His Asp Ile Tyr Lys His Leu Ile Ser Ser Pro Asn Ser
                165                 170                 175

Tyr Val Glu Ser Tyr Phe Asp Phe Glu Asp Tyr Arg Tyr Asp Pro Ile
            180                 185                 190

Met Leu Phe Ala Ile Pro Lys Asp Lys Trp Arg Lys Gly Ser Gln Trp
        195                 200                 205

Phe Thr Leu Ile Arg Arg His Ala Gln Ile Val Ala Asp Asp Asp Val
        210                 215                 220

Val Phe Pro Ile Ile Lys Lys Ser Cys Lys Arg Gln Ser Asn Ala Ser
225                 230                 235                 240

Val Ser Ala Arg Arg Gln Met Leu Asp Ile His Lys Met Gln Asp Cys
                245                 250                 255

Asn Pro Asp Glu His Tyr Leu Gln Thr Leu Leu Ala Met Ser Gly Leu
            260                 265                 270

Glu Asn Asp Phe Ser Arg Arg Ser Leu Thr Phe Thr Leu Tyr Asp Gln
        275                 280                 285

Ser Ala Thr Gln Asn Asp Lys Gln Trp His Pro Val Thr Phe Asp Tyr
        290                 295                 300

Ala Asp Ala Ser Pro Gln Ser Ile Lys Glu Ile Lys Glu Ile Glu Ala
305                 310                 315                 320

Ile Tyr Tyr Glu Ser Glu Asn Arg Thr Glu Trp Cys Gln Ile Asn Ser
                325                 330                 335

Ala Pro Ser Pro Cys Tyr Leu Phe Ala Arg Lys Phe Thr Arg Gly Ala
            340                 345                 350

Ala Val Arg Leu Leu Ser Glu Gly Leu Leu Gly Pro Phe Asp Pro Val
        355                 360                 365

Pro Phe Leu Asn Ala Thr Gly Arg Phe Phe Pro Val Lys His Arg Glu
        370                 375                 380

Thr Asp Ala Thr
385

<210> SEQ ID NO 30
<211> LENGTH: 383
<212> TYPE: PRT
<213> ORGANISM: Arabidopsis thaliana

<400> SEQUENCE: 30

Met Thr Lys Lys Ser Gln Pro Gln Ile Pro Pro Leu Ser Arg Arg
1               5                   10                  15

Gly Gly Val Val Trp Leu Gly Trp Lys Leu Val Ile Ala Phe Ser Val
            20                  25                  30

Ala Leu Cys Leu Leu Ala Leu Leu Arg Ile Gln Leu Gln Tyr Asn Ser
        35                  40                  45

Phe Thr Thr Leu Ser Phe Pro Leu Ser Val Ala Arg Ser Gln Thr Pro
    50                  55                  60
```

Leu His Lys Tyr Ser Gly Asp Arg Pro Lys Leu Ala Phe Leu Phe Leu
65                  70                  75                  80

Ala Arg Arg Asp Leu Pro Leu Asp Phe Met Trp Asp Arg Phe Phe Lys
                85                  90                  95

Gly Val Asp His Ala Asn Phe Ser Ile Tyr Ile His Ser Val Pro Gly
            100                 105                 110

Phe Val Phe Asn Glu Glu Thr Thr Arg Ser Gln Tyr Phe Tyr Asn Arg
            115                 120                 125

Gln Leu Asn Asn Ser Ile Lys Val Val Trp Gly Ser Ser Met Ile
130                 135                 140

Glu Ala Glu Arg Leu Leu Leu Ala Ser Ala Leu Glu Asp His Ser Asn
145                 150                 155                 160

Gln Arg Phe Val Leu Leu Ser Asp Arg Cys Ala Pro Leu Tyr Asp Phe
                165                 170                 175

Gly Tyr Ile Tyr Lys Tyr Leu Ile Ser Ser Pro Arg Ser Phe Val Asp
            180                 185                 190

Ser Phe Leu His Thr Lys Glu Thr Arg Tyr Ser Val Lys Met Ser Pro
            195                 200                 205

Val Ile Pro Glu Glu Lys Trp Arg Lys Gly Ser Gln Trp Ile Ala Leu
    210                 215                 220

Ile Arg Ser His Ala Glu Val Ile Val Asn Asp Gly Ile Val Phe Pro
225                 230                 235                 240

Val Phe Lys Glu Phe Cys Lys Arg Cys Pro Pro Leu Gly Thr Asn Glu
                245                 250                 255

Ala Trp Leu Phe Leu Lys Gln Lys Arg Arg Asn Cys Ile Pro Asp Glu
            260                 265                 270

His Tyr Val Gln Thr Leu Leu Thr Met Gln Gly Leu Glu Ser Glu Met
            275                 280                 285

Glu Arg Arg Thr Val Thr Tyr Thr Val Trp Asn Val Ser Gly Thr Lys
290                 295                 300

Tyr Glu Ala Lys Ser Trp His Pro Val Thr Phe Thr Leu Glu Asn Ser
305                 310                 315                 320

Gly Pro Glu Glu Ile Lys Glu Ile Lys Lys Ile Asp His Val Tyr Tyr
                325                 330                 335

Glu Ser Glu Ser Arg Thr Glu Trp Cys Lys Ala Asp Ser Lys Pro Val
            340                 345                 350

Pro Cys Phe Leu Phe Ala Arg Lys Phe Thr Asn Glu Ala Ala Met Arg
            355                 360                 365

Ile Val Ser Glu Gly Leu Ile Gly Ser Ser Ala Asn Lys Thr Leu
370                 375                 380

<210> SEQ ID NO 31
<211> LENGTH: 378
<212> TYPE: PRT
<213> ORGANISM: Arabidopsis thaliana

<400> SEQUENCE: 31

Met Pro Arg Leu Pro Ser Ser Arg Arg Gly Val Val Trp Phe Arg Trp
1               5                   10                  15

Lys Ile Leu Ile Thr Ile Ser Thr Ala Leu Cys Ile Leu Ala Leu Phe
                20                  25                  30

Cys Ile Asn Arg Gln Ser Asn Ser Thr Ala Thr Thr Thr Leu Ser
            35                  40                  45

Ser Ser Leu Ser Val Ala Arg Ser Arg Ile Pro Leu Val Lys Tyr Ser

```
            50                  55                  60
Gly Asp Arg Pro Lys Leu Ala Phe Leu Phe Leu Ala Arg Arg Asp Leu
 65                  70                  75                  80

Pro Leu Asp Phe Leu Trp Asp Arg Phe Phe Lys Ser Ala Asp Gln Arg
                 85                  90                  95

Asn Phe Ser Ile Tyr Val His Ser Ile Pro Gly Phe Val Phe Asp Glu
            100                 105                 110

Ser Ser Thr Arg Ser His Phe Phe Tyr Asn Arg Gln Leu Lys Asn Ser
        115                 120                 125

Ile Glu Val Val Trp Gly Glu Ser Ser Met Ile Ala Ala Glu Arg Leu
130                 135                 140

Leu Leu Ala Ser Ala Leu Glu Asp Pro Ser Asn Gln Arg Phe Val Leu
145                 150                 155                 160

Leu Ser Asp Ser Cys Val Pro Leu Tyr Asp Phe Gly Tyr Ile Tyr Arg
                165                 170                 175

Tyr Leu Val Ser Ser Pro Lys Ser Phe Val Asp Ser Phe Leu Asp Lys
            180                 185                 190

Asp Asn Arg Tyr Thr Met Lys Met Phe Pro Val Ile Arg Lys Glu Lys
        195                 200                 205

Trp Arg Lys Gly Ser Gln Trp Ile Ser Leu Ile Arg Ser His Ala Glu
210                 215                 220

Val Ile Val Asn Asp Asp Thr Val Phe Pro Val Phe Gln Lys Phe Cys
225                 230                 235                 240

Lys Arg Ser Leu Pro Leu Asp Pro Arg Lys Asn Trp Leu Tyr Leu Lys
                245                 250                 255

Lys Arg Arg His Asn Cys Ile Pro Asp Glu His Tyr Val Gln Thr Leu
            260                 265                 270

Leu Thr Met Arg Gly Leu Glu Asn Glu Met Glu Arg Thr Val Thr
        275                 280                 285

Tyr Thr Thr Trp Asn Leu Ser Ala Lys Lys Ala Glu Ala Lys Ser Trp
290                 295                 300

His Pro Leu Thr Phe Thr Ser Asp Asn Cys Gly Pro Glu Glu Ile Glu
305                 310                 315                 320

Gly Ile Lys Lys Ile Asn His Val Tyr Tyr Glu Ser Glu Tyr Arg Thr
                325                 330                 335

Glu Trp Cys Arg Ala Asn Ser Lys Pro Val Pro Cys Phe Leu Phe Ala
            340                 345                 350

Arg Lys Phe Thr Arg Gly Ala Ala Met Arg Leu Leu Ser Glu Gly Leu
        355                 360                 365

Ile Glu Ser Ser Ile Asp Thr Thr Thr Phe
370                 375

<210> SEQ ID NO 32
<211> LENGTH: 379
<212> TYPE: PRT
<213> ORGANISM: Amborella trichopoda

<400> SEQUENCE: 32

Met Lys Lys Arg His Ser Ala His His Leu Phe Trp Leu Gly Leu Arg
  1               5                  10                  15

Val Val Leu Gly Leu Ser Ala Thr Phe Cys Val Leu Ser Phe Leu Arg
                 20                  25                  30

Ile Gln Ser Glu Tyr Lys Pro Glu Pro Pro Phe Thr Trp Thr Gln Leu
            35                  40                  45
```

```
Pro Phe Thr Gly Pro Pro Lys Ile Ala Phe Leu Phe Leu Val Arg Ala
    50                  55                  60

Asn Leu Pro Leu Asp Phe Leu Trp Asn His Phe Phe Leu Asn Gly Asp
 65                  70                  75                  80

Ser Arg Asn Phe Ser Ile Tyr Ile His Ser Lys Pro Gly Phe Val Leu
                 85                  90                  95

Asp Glu Ser Thr Thr Arg Cys Thr Phe Cys Tyr Gly Arg Gln Leu Ser
            100                 105                 110

Gln Ser Ile Gln Val Gly Trp Gly Glu Ala Thr Met Ile Lys Ala Glu
        115                 120                 125

Arg Ile Leu Ile Gln Lys Ala Leu Gln Asp Pro Ala Asn Gln Arg Phe
130                 135                 140

Val Leu Leu Ser Glu Ser Cys Val Pro Leu Tyr Asn Phe Ser Tyr Ile
145                 150                 155                 160

Tyr Asn Tyr Leu Leu Ala Ser Pro Lys Ser Phe Val Asp Ser Phe Leu
                165                 170                 175

Asp Thr Lys Glu Gly Arg Tyr Asn Pro Lys Met Ser Ser Val Ile Pro
            180                 185                 190

Lys Asp Arg Trp Lys Lys Gly Ser Gln Trp Ile Thr Leu Ile Arg Lys
        195                 200                 205

His Ala Glu Leu Val Val Thr Asp Asp Arg Ile Phe Pro Val Phe Glu
210                 215                 220

Arg Tyr Cys Lys Arg Arg Pro Pro Ser Asp Glu Leu Glu Glu Lys Val
225                 230                 235                 240

Ser Arg Ser Phe Leu Phe Ser Phe His Lys Pro Asn Val Gln Lys Glu
                245                 250                 255

His Asn Cys Ile Pro Asp Glu His Tyr Val Gln Thr Leu Leu Ala Met
            260                 265                 270

Arg Asp Leu Glu Asp Glu Val Glu Arg Arg Thr Leu Thr Tyr Thr Ser
        275                 280                 285

Trp Asn Gln Ser Thr Thr Glu Thr Glu Lys Gln Ala Trp His Pro Leu
290                 295                 300

Thr Phe Gly Tyr Arg Asn Ala Asp Ser His Arg Ile Lys Glu Ile Lys
305                 310                 315                 320

Asp Ile Asn His Val Tyr Tyr Glu Thr Glu Tyr Arg Thr Glu Trp Cys
                325                 330                 335

Trp Arg Asn Gly Thr Ala Ala Pro Cys Phe Leu Phe Ala Arg Lys Phe
            340                 345                 350

Ser Arg Gly Ala Ala Ile Arg Leu Leu Asn Glu Gly Val Val Gly Glu
        355                 360                 365

Phe Asp Gly Ala Leu Tyr Leu Lys Pro Ser Leu
370                 375

<210> SEQ ID NO 33
<211> LENGTH: 421
<212> TYPE: PRT
<213> ORGANISM: Glycine max

<400> SEQUENCE: 33

Met Ala Ser Met Ala Arg Gly Ala Lys Arg His Ser Ile Ile Ser
 1               5                  10                  15

Arg Lys Met Leu Ile Leu Phe Ser Ala Ser Leu Ser Cys Val Val Val
                 20                  25                  30

Leu Val Ile Cys Ser Leu Phe Arg Phe His Ser Pro Lys Pro Pro Ile
             35                  40                  45
```

```
Ser Ile Ser Ile Ser Arg Val Val Phe Asp Gly Pro Pro Lys Ile Ala
         50                  55                  60

Phe Leu Phe Leu Val Arg Arg Asn Leu Pro Leu Asp Phe Leu Trp Asp
 65                  70                  75                  80

Ala Phe Phe Gln Asn Val Asp Val Ser Arg Phe Ser Ile Tyr Val His
                 85                  90                  95

Ser Ala Pro Gly Phe Val Leu Asp Glu Ser Thr Thr Arg Ser Gln Phe
            100                 105                 110

Leu Tyr Gly Arg Gln Ile Ser Asn Ser Ile Gln Val Leu Trp Gly Glu
        115                 120                 125

Ser Ser Met Ile Gln Ala Glu Arg Leu Leu Leu Ala Ala Ala Leu Glu
    130                 135                 140

Asp Pro Ala Asn Gln Arg Phe Val Leu Leu Ser Asp Ser Cys Val Pro
145                 150                 155                 160

Leu Tyr Asn Phe Ser Tyr Val Tyr Asn Tyr Leu Met Val Ser Pro Arg
                165                 170                 175

Ser Phe Val Asp Ser Phe Leu Asp Ala Lys Glu Gly Arg Tyr Asn Pro
            180                 185                 190

Lys Met Ser Pro Lys Ile Pro Arg Glu Lys Trp Arg Lys Gly Ser Gln
        195                 200                 205

Trp Ile Thr Val Val Arg Lys His Ala Glu Val Val Val Asp Asp Asp
    210                 215                 220

Val Ile Phe Ser Val Phe Lys Lys Tyr Cys Lys Arg Arg Pro Pro Ile
225                 230                 235                 240

Asp Thr Ser Lys Gly Lys Leu Asn Leu Lys Leu Gln Lys Gln His Asn
                245                 250                 255

Cys Ile Pro Asp Glu His Tyr Val Gln Thr Leu Leu Ala Met His Asp
            260                 265                 270

Leu Glu Gly Glu Leu Glu Arg Arg Thr Leu Thr Tyr Thr Leu Trp Asn
        275                 280                 285

Gln Ser Thr Thr Lys Met Glu Asn Lys Gly Trp His Pro Ile Thr Phe
    290                 295                 300

Gly Tyr Ser Asn Ala Ser Pro Gln Arg Ile Lys Glu Ile Lys Gly Ile
305                 310                 315                 320

Asn His Val Tyr Tyr Glu Thr Glu Tyr Arg Ile Glu Trp Cys His Thr
                325                 330                 335

Asn Ser Thr Ser Val Pro Cys Phe Leu Phe Ala Arg Lys Phe Ser Gln
            340                 345                 350

Gly Ala Ala Met Arg Leu Leu Ser Gln Glu Val Val Asn His Phe Glu
        355                 360                 365

Val Ser Ala Leu His Ile Leu Gln Thr Ala Asn Gly Ile Thr Thr Ser
    370                 375                 380

Phe Asn Arg His Thr Pro His Lys Asp Phe Asp Gly Ile Ile Gln
385                 390                 395                 400

His Thr Pro His Lys Gln Ile Leu Lys Thr Lys Ile Gly Gln Val Ser
                405                 410                 415

Ala Asp Arg Met Leu
            420

<210> SEQ ID NO 34
<211> LENGTH: 377
<212> TYPE: PRT
<213> ORGANISM: Glycine max
```

<400> SEQUENCE: 34

```
Met Ala Ser Met Ala Arg Gly Ala Lys Arg Arg His Ala Val Ile Ser
1               5                   10                  15

Lys Lys Met Leu Ile Leu Phe Ser Ala Ser Leu Ser Cys Val Val Val
            20                  25                  30

Leu Val Ile Phe Ser Leu Phe Arg Phe His Ser Pro Lys Pro Pro Ile
        35                  40                  45

Ser Ile Ser Ile Ser Arg Val Val Phe Asp Gly Pro Pro Lys Ile Ala
    50                  55                  60

Phe Leu Phe Leu Val Arg Arg Asn Leu Pro Leu Asp Phe Leu Trp Asp
65                  70                  75                  80

Ala Phe Phe Gln Asn Gly Asp Val Ser Arg Phe Ser Ile Tyr Val His
                85                  90                  95

Ser Ala Pro Gly Phe Val Leu Asp Glu Ser Thr Thr Arg Ser Gln Leu
            100                 105                 110

Phe Tyr Gly Arg Gln Ile Ser Asn Ser Ile Gln Val Leu Trp Gly Glu
        115                 120                 125

Ser Ser Met Ile Gln Ala Glu Arg Leu Leu Leu Ala Ala Ala Leu Glu
    130                 135                 140

Asp His Ala Asn Gln Arg Phe Val Leu Leu Ser Asp Ser Cys Val Pro
145                 150                 155                 160

Leu Tyr Asn Phe Ser Tyr Val Tyr Asn Tyr Leu Met Val Ser Pro Arg
                165                 170                 175

Ser Phe Val Asp Ser Phe Leu Asp Ala Lys Glu Gly Arg Tyr Asn Pro
            180                 185                 190

Lys Met Ser Thr Lys Ile Pro Arg Glu Lys Trp Arg Lys Gly Ser Gln
        195                 200                 205

Trp Ile Thr Val Val Arg Lys His Ala Glu Val Ile Val Asp Asp Asp
    210                 215                 220

Val Ile Phe Ser Val Phe Lys Lys Tyr Cys Lys Arg Arg Pro Pro Ile
225                 230                 235                 240

Asp Thr Ser Lys Gly Lys Leu Asn Leu Lys Leu Gln Lys Gln His Asn
                245                 250                 255

Cys Ile Pro Asp Glu His Tyr Val Gln Thr Leu Leu Ala Met His Asp
            260                 265                 270

Leu Glu Gly Glu Leu Glu Arg Arg Thr Leu Thr Tyr Thr Leu Trp Asn
        275                 280                 285

Gln Ser Thr Thr Lys Met Glu Asn Lys Gly Trp His Pro Ile Thr Phe
    290                 295                 300

Gly Tyr Ser Asn Ala Ser Pro Gln Arg Ile Lys Glu Ile Lys Gly Ile
305                 310                 315                 320

Asn His Val Tyr Tyr Glu Thr Glu Tyr Arg Ile Glu Trp Cys His Thr
                325                 330                 335

Asn Ser Thr Ser Val Pro Cys Phe Leu Phe Ala Arg Lys Phe Ser Gln
            340                 345                 350

Gly Ala Ala Met Arg Leu Leu Ser Gln Glu Val Val Asn His Phe Glu
        355                 360                 365

Val Ser Ala Leu Leu Ala Thr Pro Thr
    370                 375
```

<210> SEQ ID NO 35
<211> LENGTH: 385
<212> TYPE: PRT
<213> ORGANISM: Eucalyptus grandis

<400> SEQUENCE: 35

```
Met Lys Lys Ser Ala Gln Val Ala Ala Arg His Val Leu Trp Leu
  1               5                  10                  15

Gly Trp Lys Leu Val Ile Leu Leu Ser Leu Ser Leu Cys Leu Leu Ala
             20                  25                  30

Leu Phe Arg Leu His Ser Pro Pro Asn Tyr Tyr Ser Ser Ser Ser Ser
         35                  40                  45

Thr Ser Pro His Leu Asp Val Leu Arg Arg Gly Ala Gly Ser Arg
     50                  55                  60

Phe Ala Gly Thr Pro Lys Leu Ala Phe Leu Phe Leu Ala Arg Arg Asn
 65                  70                  75                  80

Leu Pro Leu Asp Phe Leu Trp Gly Ser Phe Phe Glu Asn Ala Asp Ala
                 85                  90                  95

Ala Asn Phe Ser Ile Tyr Ile His Ser Glu Pro Gly Phe Val Phe Asp
                100                 105                 110

Ala Thr Thr Thr Arg Ser Arg Phe Phe Tyr Gly Arg Gln Leu Arg Asn
            115                 120                 125

Ser Ile Gln Val Gly Trp Gly Glu Ser Ser Met Ile Glu Ala Glu Arg
    130                 135                 140

Leu Leu Phe Ala Ala Ala Leu Glu Asp Pro Ala Asn Gln Arg Leu Val
145                 150                 155                 160

Leu Leu Ser Asp Ser Cys Val Pro Leu Tyr Asn Phe Ser Tyr Ile Tyr
                165                 170                 175

Ser Tyr Leu Met Ala Ser Ser Arg Ser Phe Val Asp Ser Phe Leu Asp
            180                 185                 190

Ala Lys Glu Gly Arg Tyr Asn Pro Gln Met Phe Pro Val Ile Pro Lys
        195                 200                 205

Glu Arg Trp Arg Lys Gly Ser Gln Trp Ile Ala Leu Val Arg Lys His
210                 215                 220

Ala Glu Val Val Val Asp Asp Glu Val Val Phe Pro Ala Phe Lys Lys
225                 230                 235                 240

Phe Cys Lys Arg Arg Pro Pro Val Asp Ala Ser Lys Gly Lys Leu Asn
                245                 250                 255

Thr Lys Leu Gln Lys Gln His Asn Cys Ile Pro Asp Glu His Phe Val
            260                 265                 270

Gln Thr Leu Leu Ser Leu Asn Glu Leu Asp Thr Glu Leu Glu Arg Arg
        275                 280                 285

Thr Val Thr Tyr Thr Ser Trp Asn Gln Ser Ala Thr Lys Met Asp Thr
    290                 295                 300

Lys Gly Trp His Pro Val Thr Phe Asp Tyr Ala Asn Ala Ser Pro Arg
305                 310                 315                 320

Gln Ile Gln Gly Ile Lys Lys Ile Asn His Val Tyr Tyr Glu Thr Glu
                325                 330                 335

Phe Arg Thr Glu Trp Cys Arg Ala Asn Leu Ser Ser Val Pro Cys Phe
            340                 345                 350

Leu Phe Ala Arg Lys Phe Ser Arg Gly Ala Ala Met Arg Leu Leu Ser
        355                 360                 365

Glu Gly Val Val Gly Arg Phe Asp Ala Ser Ser Leu Leu Asp Ser Thr
    370                 375                 380

Pro
385
```

<210> SEQ ID NO 36
<211> LENGTH: 380
<212> TYPE: PRT
<213> ORGANISM: Vitis vinifera

<400> SEQUENCE: 36

```
Met Thr Lys Lys Ala Pro Ser Phe Ser Ile Arg His Val Phe Trp Phe
1               5                   10                  15

Gly Trp Lys Leu Val Ile Leu Val Ser Val Ala Leu Cys Val Leu Ala
            20                  25                  30

Leu Leu Arg Leu Gln Ser Asn Ser Glu Leu Ser Ser Ile Ser Leu Pro
        35                  40                  45

Pro Gln Gly Pro Arg Phe Tyr Arg Val Ser Val Tyr Gln Gly Asn Pro
    50                  55                  60

Lys Ile Ala Phe Leu Phe Leu Val Arg Arg Ser Leu Pro Leu Asp Phe
65                  70                  75                  80

Leu Trp Gly Ser Phe Phe Glu Asn Ala Asp Ala Ala Asn Phe Ser Ile
                85                  90                  95

Tyr Ile His Ser Gln Pro Gly Phe Val Phe Asp Glu Thr Thr Ser Arg
            100                 105                 110

Ser Arg Phe Phe Tyr Asn Arg Gln Leu Ser Asn Ser Ile Gln Val Ala
        115                 120                 125

Trp Gly Glu Ser Ser Met Ile Gln Ala Glu Arg Leu Leu Phe Glu Ala
    130                 135                 140

Ala Leu Glu Asp Pro Ala Asn Gln Arg Phe Val Leu Leu Ser Asp Ser
145                 150                 155                 160

Cys Val Pro Leu Tyr Asn Phe Ser Tyr Ile Tyr Asn Tyr Met Met Ala
                165                 170                 175

Ser Pro Arg Ser Tyr Val Asp Ser Phe Leu Asp Val Lys Glu Gly Arg
            180                 185                 190

Tyr Asn Pro Lys Met Ser Pro Val Ile Pro Lys Ala Lys Trp Arg Lys
        195                 200                 205

Gly Ser Gln Trp Ile Ser Leu Val Arg Ser His Ala Glu Val Ile Val
    210                 215                 220

Asp Asp Gln Val Ile Phe Ser Val Phe Lys Lys Phe Cys Lys Arg Arg
225                 230                 235                 240

Pro Pro Ile Asp Ala Arg Lys Gly Lys Gln Asn Ile Lys Leu Gln Lys
                245                 250                 255

Gln His Asn Cys Ile Pro Asp Glu His Tyr Val Gln Thr Leu Leu Ala
            260                 265                 270

Met Ser Glu Leu Glu Ser Glu Leu Glu Arg Arg Thr Leu Thr Tyr Thr
        275                 280                 285

Glu Trp Asn Leu Ser Val Thr Lys Met Glu Arg Glu Gly Trp His Pro
    290                 295                 300

Ile Thr Phe Ser Tyr Ala Asn Ala Gly Pro Gln Arg Ile Lys Glu Ile
305                 310                 315                 320

Lys Asp Val Asn His Val Tyr Tyr Glu Thr Glu Phe Arg Thr Glu Trp
                325                 330                 335

Cys Arg Ala Asn Ser Thr Ser Val Pro Cys Phe Leu Phe Ala Arg Lys
            340                 345                 350

Phe Ser Arg Gly Ala Ala Met Arg Leu Leu Ser Glu Gly Val Val Gly
        355                 360                 365

Ser Phe Asp Val Thr Ala Phe Asp Ala Pro Ser
    370                 375                 380
```

<210> SEQ ID NO 37
<211> LENGTH: 1161
<212> TYPE: DNA
<213> ORGANISM: Populus Trichocarpa

<400> SEQUENCE: 37

| | | | | | | |
|---|---|---|---|---|---|---|
| atgacaaaga | aatcatcatt | gctgccgatt | cttcttcaac | agtcaagacg | acgtgtcatc | 60 |
| tggtctggat | ggaagctagt | gatcatcctc | tccatgggc | tctgtgtttt | tgctctttt | 120 |
| agaattcatt | tatcttctcc | tcctgaaact | ttactttctc | gtagaagatc | tttttctcgc | 180 |
| gaagttgtct | tcagtggccc | ccctaaagtc | gcctttcttt | ttcttgttag | acggggcttg | 240 |
| cctcttgatt | ttctctgggg | gagtttcttt | gagaatgctg | acacggggaa | ttttcgata | 300 |
| catgtacact | cagagccagg | gtttgagttt | gatgagtcaa | caacaaggtc | acattctt | 360 |
| tatggtcgac | aattgaagaa | cagtattcag | gtaatatggg | gagaatcaag | tatgatagaa | 420 |
| gcagaaaggt | tactacttga | tgctgcttta | gaggatccag | caaatcaaag | atttgttctt | 480 |
| ctctctgaca | gttgtgtgcc | tttatacaac | tttagctata | tatacagcta | tttgatggct | 540 |
| tctcctagga | gttttgtgga | cagctttctt | gatgtgaagg | aaggccgcta | ccaccctaag | 600 |
| atgtcacctg | ttataccaaa | ggacaagtgg | cgaaaagggt | cccagtggat | agctttaatc | 660 |
| cggagccatg | ctgaagtgat | tgtagatgat | gttgttatct | taccagtctt | taagaaactt | 720 |
| tgcaagcgtc | gcccgcctct | tgatgccagt | aagggaaagc | tgaatattaa | acttcagaag | 780 |
| caacacaact | gtattcctga | tgaacactat | gtgcagacat | gctttcgat | gagtgaacta | 840 |
| gagggtgaac | ttgaaagaag | gaccgtgacc | tatactgtat | ggaatcaatc | cgcaacaaaa | 900 |
| atggaaaaca | aaggctggca | tcctaagaca | ttttcctatg | caaatgcaag | ccctcggaaa | 960 |
| atcaaggaaa | taagggcat | caaccatata | gactatgaga | ccgagtaccg | aacagaatgg | 1020 |
| tgccggacta | actcaacatt | cgttccttgt | ttctattcg | cacggaagtt | ctcacgagga | 1080 |
| gctgccatgc | gcctattgag | tgatggtgtt | gctggtcaat | tgatgcctc | ttccatatta | 1140 |
| gccaggtctg | cccctgatta | g | | | | 1161 |

<210> SEQ ID NO 38
<211> LENGTH: 4487
<212> TYPE: DNA
<213> ORGANISM: Populus Trichocarpa

<400> SEQUENCE: 38

| | | | | | | |
|---|---|---|---|---|---|---|
| ttcccattcc | cattgtcatt | tcgtattttt | cttacactga | cacaaacgaa | agctcttaca | 60 |
| gatcaagcaa | acattaaaaa | cttcaaagaa | gcaaatccca | tgtccctctc | tcaaaatcaa | 120 |
| tgtaataaca | atttaataa | ttatattaat | aataatattt | aatttccctt | ttcatttcat | 180 |
| tttcttatgt | aattattttc | attattttcg | ttctttttct | tgttttgat | aggaaggagg | 240 |
| agaaggatga | caaagaaatc | atcattgctg | ccgattcttc | ttcaacagtc | aagacgacgt | 300 |
| gtcatctggt | ctggatggaa | gctagtgatc | atcctctcca | tggggctctg | tgttttgct | 360 |
| cttttagaa | ttcatttatc | ttctcctcct | gaaactttac | tttctcgtag | aagatcttt | 420 |
| tctcgcgaag | ttgtcttcag | tggccccct | aaagtcgcct | ttctttttct | tgttagacgg | 480 |
| ggcttgcctc | ttgatttct | ctggggagt | tctttgagg | taattaaaaa | gaaaaatggc | 540 |
| aactttttga | tcttttttg | aattttgatt | tgaatttttt | gagttttctt | tcactttccc | 600 |
| gggaaagctg | gtggaatttg | gaatagggt | tttattttt | attttagtt | tgtgatttga | 660 |
| ttttctgtc | actttctttg | gaaagtaatg | gaatttggga | agagcgtttg | ttttacaatg | 720 |

```
caatttgtgt tttctgtcac tttctcgaga aaattaactg aatttaggtt tatgtgtgta    780
tttgaatctt ctttcagaaa gttaacggaa tttaggaaat gggatttgat ttttgtgttg    840
attacaattt gagccttctg tcagtttctc aggaaaatta atggaatttg gaaaattggg    900
ttctaatgtt tttgcagaat gctgacacgg ggaatttttc gatacatgta cactcagagc    960
cagggtttga gtttgatgag tcaacaacaa ggtcacattt cttttatggt cgacaattga   1020
agaacagtat tcaggtcact tatcaataaa agcttctaaa gattcaactt ttttccattt   1080
tagtaaattg tgcacgaaat ggctactgga aagtacaaat ttgcatcgca ttatttctat   1140
cttttcttat ttcccccatt gtcagtgcct aaagtggttc actaggtttc atttggtcaa   1200
aatatgagtc ctttggagtt ggacagatgg aattgataga tgtatatttt ttttaattgg   1260
cttatgcaag caataggtaa acacagttta aatattcgcg ctttattgtc ttttgaaaat   1320
ttctactaat gtagcgtgtt aatgttaact ttgattttgt taaagttaga cttttttctt   1380
taagcgaaaa aggaatgatg gataatatat tgtatgtttg aaattggaat tttgcaggta   1440
atatggggag aatcaagtat gatagaagca gaaaggttac tacttgatgc tgctttagag   1500
gatccagcaa atcaaagatt tgttcttctc tctgacaggt tgatttcctg tattgagttg   1560
gtcaatgaat tgttcaaca aagcttgtgt ttagaccttt gcaacttatt tccttattta   1620
tcgattatcc tttttaata gtttcattac cttattaggc acgtgagttg aattcatgtg   1680
gcgagtttca tgtctaaaac atgtaatgtt ctttatttgt atgttgcagt tgtgtgcctt   1740
tatacaactt tagctatata tacagctatt tgatggcttc tcctaggagt tttgtggaca   1800
ggtaatcgga agggctttca ttcttgaggt gccaagcatt gattgtatta ccattcagcc   1860
tttgacctct ttgtagtgtt tatgaaggaa tcttgaaaag ctaagattta tttatatgct   1920
ttgtgttaca gctttcttga tgtgaaggaa ggccgctacc accctaagat gtcacctgtt   1980
ataccaaagg acaagtggcg aaaagggtcc caggttgttc cataaagaaa caagtttatc   2040
ttcctatgtg atctttatgc ataaacaatg ctttaacttg acatttgatt ttgtaattac   2100
agtggatagc tttaatccgg agccatgctg aagtgattgt agatgatgtt gttatcttac   2160
cagtctttaa gaaactttgc aaggtacttg atcaagttat tttgtccata gctgcaactt   2220
cattttcaga tataatagat atttaaacca ttaatgctgc ttatgtaaga tgtgactatt   2280
tctgaaactt gactaacttt gctatgcagc aacatgtatg ctgctgtagt gaatggagct   2340
ttcttaaaac ctaaaatgat ttaaattgac gagcaagaca atatattacc tttagaattt   2400
actactttat tttgatgatg ctcaccttt catcatgtgt aattggacct ttttcccatt   2460
actaaatgac ttgctcctct ttaattttgc tggcatgatt tttgtccata tatctgcgca   2520
agcattgttc ttcttcctgg ttggttctaa ttccttacag acaattctaa ctagatgcaa   2580
ccactgtcga aaagctttta aaatctgtat taatcatgta ataacttact tttaacatct   2640
gtacattttg cagcgtcgcc cgcctcttga tgccagtaag ggaaagctga atattgtaag   2700
ttatattcaa catctaattt tctacattgt aaggaaaaat gcttcttaat gttctgatat   2760
ttgaatcctc ttgtcttatg ttgagtttaa ttcatatgtt tggcccttgc ctgcctgtag   2820
```

```
cttctggagc tattggaaat gttctttcta tggtgaattc tgtctcatag ctgtgttcaa    2880
ctcatatact atgcctttgc caactgcaga tcgtaatata tttgttgtac cttaagggtg    2940
ttggcttatt gtcatttcta gttactgttt gctcaattat ctttggttgc ttcagtataa    3000
tgaagcaaca atgtacattt gcaaaatagc aaagagagga gttccagtta aggcttggat    3060
attttggaaa acttcaagtt ggggcttgtt gattttcaat aattttgtgg atgtttgaaa    3120
taatttatat tcctgatatt gtgattcatc ctagtttctt tcaaggattt gatcattatt    3180
ctgatctggg cctaatcaca atgcagaaac ttcagaagca acacaactgt attcctgatg    3240
aacactatgt gcagacattg ctttcggtaa gtagcatttg gttttgtttc tacccattgt    3300
tgtcttcaga tctctgccta attgtgtttt ttttttctt ttctatgtca acttctcaga    3360
tgagtgaact agagggtgaa cttgaaagaa ggaccgtgac ctatactgta tggaatcaat    3420
ccgcaacaaa aatggaaaac aaaggctggc atcctaagac attttcctat gcaaatgcaa    3480
gccctcggaa aatcaaggaa ataaaggtca ttatttcatt tctattgtta atttagttcg    3540
atgtaatgat ggaaagcata atatggtcat atggaattct tccatctcta ttatgttatc    3600
ttatcttgga acttgaggga tcccattttg tgtgcatggg aatgctggta ccatcactat    3660
gttatctatg cgtttggaat tgtgctgtaa cttctgagga agtgtttgat ttctatcgca    3720 aaaaagaag tgcatttagg cattccatct acattctatg gttgtttttg taccactttt    3780
tagccactgg aatggtttgc gctgattctg ttttctagaa agtggtgtgg ttttcttggt    3840
tatcatatgt gcttctctca ctttctacta actcttctgt tcatctgtgt tactcaattt    3900
cacagggcat caaccatata gactatgaga ccgagtaccg aacagaatgg tgccggacta    3960
actcaacatt cgttccttgt tttctattcg cacggaagtt ctcacgagga gctgccatgc    4020
gcctattgag tgatggtgtt gctggtcaat ttgatgcctc ttccatatta gccaggtctg    4080
cccctgatta ggaacagtga catttctctc agtactattg gccctcaacc tacccatttc    4140
acaaacagtc gcggcagcta gagcacgccc acgtataaac acatgattct atacatagat    4200
tagatatcca tacaatagta gaagaatatt atctgctgct gctgattaat tttcaaggaa    4260
atgagttaga agttaacatt ttgagttttg atcctatcat taaggtctct tagcattctg    4320
atctttacat ggtttacaga ggtgggaaac taatccttgt tctgtctgcg cagtgctact    4380
gttgtagaaa gagaattttg tttcattact tgaataattg acatgctact ttataagaga    4440
ttatttaaca atgacttaaa atcacattta tttattttt ccaatct                  4487
```